United States Patent
Prior

(10) Patent No.: US 10,980,540 B2
(45) Date of Patent: Apr. 20, 2021

(54) SPRING LOADED ANVIL RETAINER

(71) Applicant: Covidien LP, Mansfield, MA (US)

(72) Inventor: Scott J. Prior, Shelton, CT (US)

(73) Assignee: Covidien LP, Mansfield, MA (US)

( * ) Notice: Subject to any disclaimer, the term of this patent is extended or adjusted under 35 U.S.C. 154(b) by 123 days.

(21) Appl. No.: 16/409,258

(22) Filed: May 10, 2019

(65) Prior Publication Data

US 2019/0261993 A1 Aug. 29, 2019

Related U.S. Application Data

(63) Continuation of application No. 15/148,619, filed on May 6, 2016, now Pat. No. 10,285,701, which is a continuation of application No. 13/871,431, filed on Apr. 26, 2013, now Pat. No. 9,351,734.

(60) Provisional application No. 61/661,464, filed on Jun. 19, 2012.

(51) Int. Cl.
A61B 17/10 (2006.01)
A61B 17/115 (2006.01)
A61B 17/11 (2006.01)
A61B 17/064 (2006.01)
A61B 17/00 (2006.01)
(Continued)

(52) U.S. Cl.
CPC .......... *A61B 17/105* (2013.01); *A61B 17/064* (2013.01); *A61B 17/115* (2013.01); *A61B 17/1114* (2013.01); *A61B 17/1155* (2013.01); *A61B 2017/00398* (2013.01); *A61B 2017/00477* (2013.01); *A61B 2017/00734* (2013.01); *A61B 2017/07235* (2013.01); *A61B 2017/07242* (2013.01); *A61B 2017/1132* (2013.01); *A61B 2017/2916* (2013.01)

(58) Field of Classification Search
CPC ... A61B 17/068; A61B 17/072; A61B 17/115; A61B 17/105
USPC ......... 227/175.1, 175.2, 176.1, 178.1, 179.1, 227/180.1, 181.1
See application file for complete search history.

(56) References Cited

U.S. PATENT DOCUMENTS 3,193,165 A 7/1965 Akhalaya et al.
3,388,847 A 6/1968 Kasulin et al.
3,552,626 A 1/1971 Astafiev et al.
(Continued)

FOREIGN PATENT DOCUMENTS

CA 908529 A 8/1972
DE 1057729 B 5/1959
(Continued)

OTHER PUBLICATIONS

European Search Report dated Sep. 25, 2013 in European Appln. No. 13 17 2397.
(Continued)

*Primary Examiner* — Nathaniel C Chukwurah

(57) ABSTRACT

A surgical stapling device includes a handle assembly, a body portion extending distally from the handle assembly, a head portion including an anvil retainer and a shell assembly. The anvil retainer is movable in relation to the shell assembly between unapproximated and approximated positions. A tube surrounds a portion of the anvil retainer, wherein the anvil retainer includes a distal annular protrusion for releasably engaging an anvil assembly and wherein the anvil assembly includes a center rod.

20 Claims, 22 Drawing Sheets

(51) Int. Cl.
     *A61B 17/29*     (2006.01)
     *A61B 17/072*    (2006.01)

(56) References Cited

U.S. PATENT DOCUMENTS

| | | |
|---|---|---|
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |

(56) References Cited

U.S. PATENT DOCUMENTS

| | | |
|---|---|---|
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma |
| 6,942,675 B1 | 9/2005 | Vargas |
| 6,945,444 B2 * | 9/2005 | Gresham ............... A61B 17/115 227/175.1 |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Willman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |

(56) References Cited

U.S. PATENT DOCUMENTS

| | | | |
|---|---|---|---|
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 9,351,734 B2 | 5/2016 | Prior |
| 10,285,701 B2 | 5/2019 | Prior |
| 2003/0111507 A1 | 6/2003 | Nunez |
| 2005/0051597 A1 | 3/2005 | Toledano |
| 2005/0107813 A1 | 5/2005 | Gilete Garcia |
| 2005/0116009 A1 * | 6/2005 | Milliman ............ A61B 17/072 227/176.1 |
| 2005/0125009 A1 | 6/2005 | Perry et al. |
| 2005/0145674 A1 | 7/2005 | Sonnenschein et al. |
| 2005/0145675 A1 | 7/2005 | Hartwick et al. |
| 2006/0000869 A1 | 1/2006 | Fontayne |
| 2006/0011698 A1 | 1/2006 | Okada et al. |
| 2006/0047307 A1 | 3/2006 | Ortiz et al. |
| 2006/0097025 A1 | 5/2006 | Milliman et al. |
| 2006/0144897 A1 | 7/2006 | Jankowski et al. |
| 2006/0201989 A1 | 9/2006 | Ojeda |
| 2006/0241692 A1 | 10/2006 | McGuckin et al. |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0173767 A1 | 7/2009 | Milliman |
| 2009/0230170 A1 | 9/2009 | Milliman |
| 2009/0236392 A1 | 9/2009 | Cole et al. |
| 2009/0236398 A1 | 9/2009 | Cole et al. |
| 2009/0236401 A1 | 9/2009 | Cole et al. |
| 2009/0255976 A1 | 10/2009 | Marczyk et al. |
| 2009/0302089 A1 | 12/2009 | Harari et al. |
| 2010/0001037 A1 | 1/2010 | Racenet et al. |
| 2010/0019016 A1 | 1/2010 | Edoga et al. |
| 2010/0038401 A1 | 2/2010 | Milliman |
| 2010/0051668 A1 | 3/2010 | Milliman et al. |
| 2010/0065607 A1 | 3/2010 | Orban, III et al. |
| 2010/0084453 A1 | 4/2010 | Hu |
| 2010/0089971 A1 | 4/2010 | Milliman et al. |
| 2010/0108739 A1 | 5/2010 | Holsten et al. |
| 2010/0108740 A1 | 5/2010 | Pastorelli et al. |
| 2010/0108741 A1 | 5/2010 | Hessler et al. |
| 2010/0133319 A1 | 6/2010 | Milliman et al. |
| 2010/0147923 A1 | 6/2010 | D'Agostino et al. |
| 2010/0163598 A1 | 7/2010 | Belzer |
| 2010/0170932 A1 | 7/2010 | Wenchell et al. |
| 2010/0224668 A1 | 9/2010 | Fontayne et al. |
| 2010/0230465 A1 | 9/2010 | Smith et al. |
| 2010/0230466 A1 | 9/2010 | Criscuolo et al. |
| 2010/0230467 A1 | 9/2010 | Criscuolo et al. |
| 2010/0258611 A1 | 10/2010 | Smith et al. |
| 2010/0264195 A1 | 10/2010 | Bettuchi |
| 2010/0270356 A1 | 10/2010 | Holsten et al. |
| 2010/0282815 A1 | 11/2010 | Bettuchi et al. |
| 2010/0301098 A1 | 12/2010 | Kostrzewski |
| 2010/0327041 A1 | 12/2010 | Milliman et al. |
| 2011/0006100 A1 | 1/2011 | Milliam |
| 2011/0006102 A1 | 1/2011 | Kostrzewski |
| 2011/0011916 A1 | 1/2011 | Levine |
| 2011/0017800 A1 | 1/2011 | Viola |
| 2011/0024476 A1 | 2/2011 | Bettuchi et al. |
| 2011/0024481 A1 | 2/2011 | Bettuchi et al. |
| 2011/0036889 A1 | 2/2011 | Heinrich et al. |
| 2011/0036894 A1 | 2/2011 | Bettuchi |
| 2011/0042442 A1 | 2/2011 | Viola et al. |
| 2011/0042443 A1 | 2/2011 | Milliman et al. |
| 2011/0057016 A1 | 3/2011 | Bettuchi |
| 2011/0089219 A1 | 4/2011 | Hessler |
| 2011/0095067 A1 | 4/2011 | Ohdaira |
| 2011/0095068 A1 | 4/2011 | Patel |
| 2011/0095069 A1 | 4/2011 | Patel et al. |
| 2011/0095070 A1 | 4/2011 | Patel et al. |
| 2011/0101065 A1 | 5/2011 | Milliman |
| 2011/0114697 A1 | 5/2011 | Baxter, III et al. |
| 2011/0114698 A1 | 5/2011 | Baxter, III et al. |
| 2011/0114699 A1 | 5/2011 | Baxter, III et al. |
| 2011/0114700 A1 | 5/2011 | Baxter, III et al. |
| 2011/0114701 A1 | 5/2011 | Hessler |
| 2011/0118761 A1 | 5/2011 | Baxter, III |
| 2011/0130788 A1 | 6/2011 | Orban, III et al. |
| 2011/0139852 A1 | 6/2011 | Zingman |
| 2011/0139853 A1 | 6/2011 | Viola |
| 2011/0144640 A1 | 6/2011 | Heinrich et al. |
| 2011/0147432 A1 | 6/2011 | Heinrich et al. |
| 2011/0147434 A1 | 6/2011 | Hueil et al. |
| 2011/0147435 A1 | 6/2011 | Heinrich et al. |
| 2011/0192882 A1 | 8/2011 | Hess et al. |
| 2011/0210156 A1 | 9/2011 | Smith et al. |
| 2011/0220703 A1 | 9/2011 | Orban, III |
| 2011/0248067 A1 | 10/2011 | Takei |
| 2012/0150221 A1 | 6/2012 | Viola |

FOREIGN PATENT DOCUMENTS

| | | |
|---|---|---|
| DE | 3301713 A1 | 7/1984 |
| EP | 0152382 A2 | 8/1985 |
| EP | 0173451 A2 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2153781 A2 | 2/2010 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 0154594 A1 | 8/2001 |
| WO | 2008107918 A1 | 9/2008 |

OTHER PUBLICATIONS

Australian Patent Examination Report No. 1, dated Nov. 15, 2016, corresponding to Australian Application No. 2013205802; 3 pages.

* cited by examiner

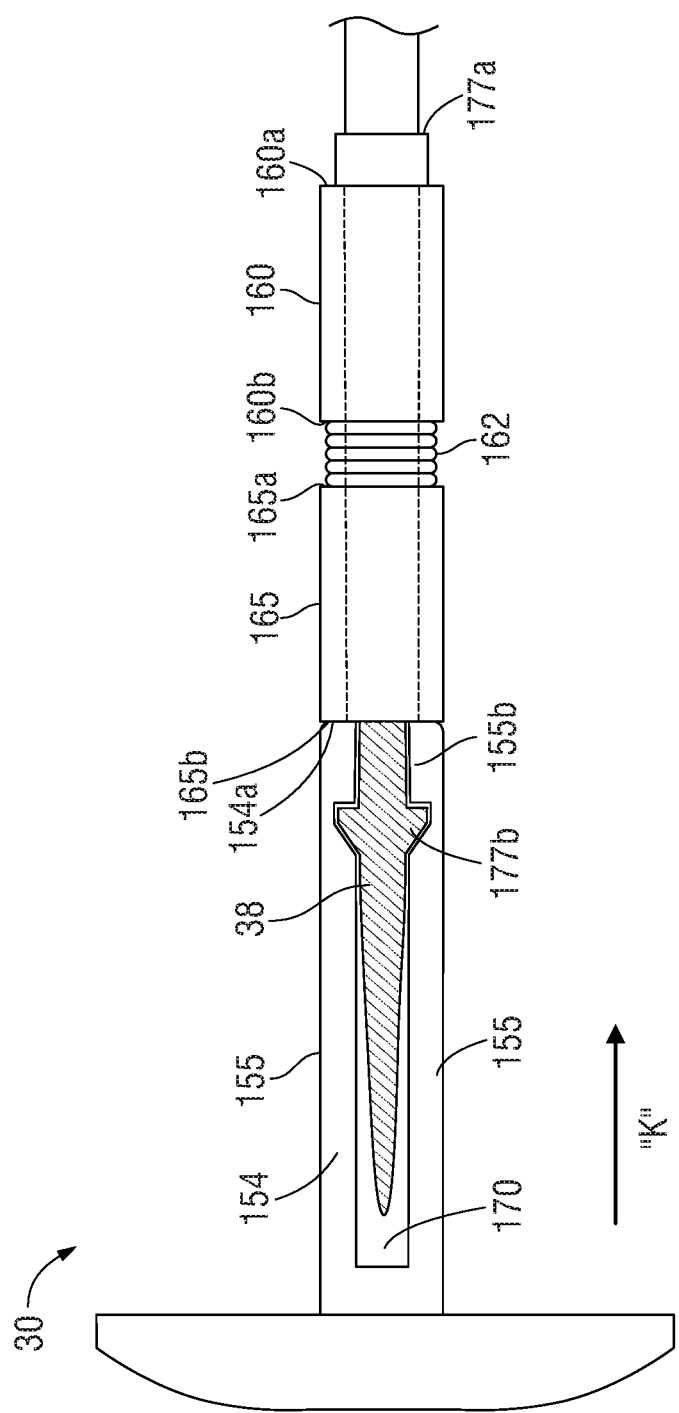

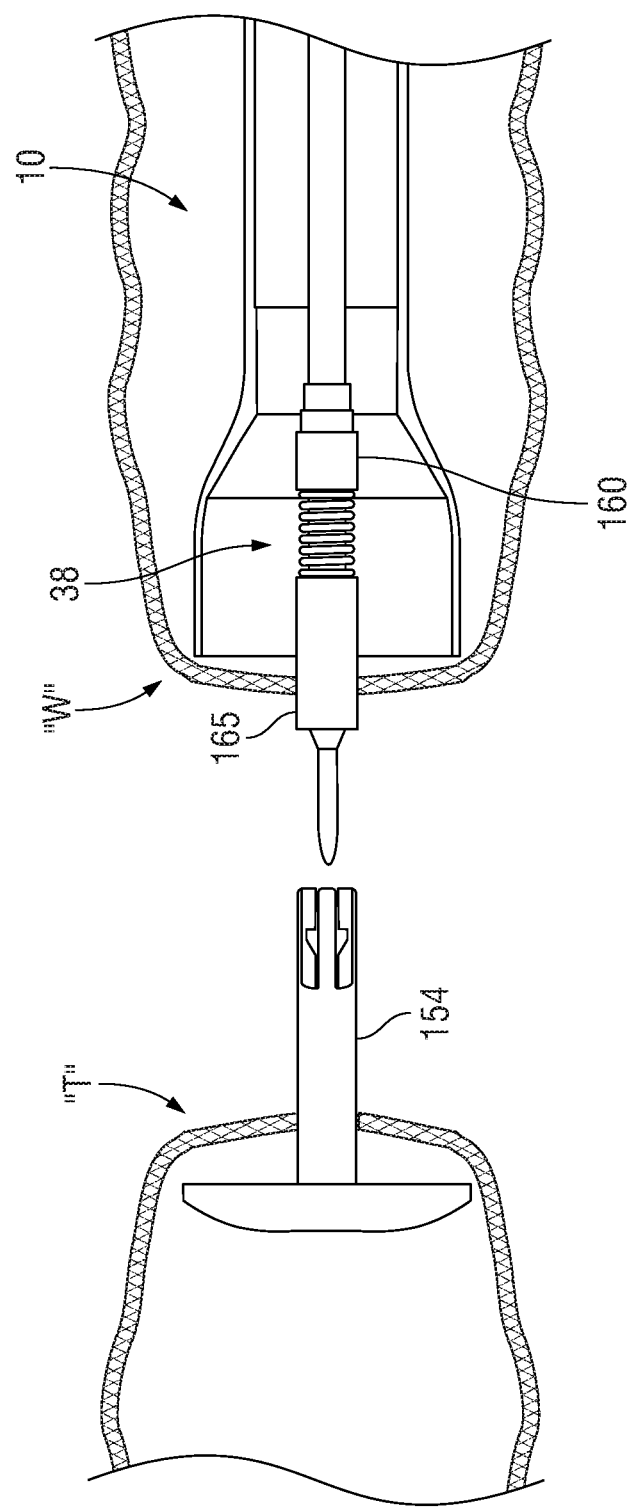

SPRING LOADED ANVIL RETAINER

CROSS-REFERENCE TO RELATED APPLICATIONS

This application is a continuation application of U.S. patent application Ser. No. 15/148,619, filed on May 6, 2016, now U.S. Pat. No. 10,285,701, which is a continuation application of U.S. patent application Ser. No. 13/871,431, now U.S. Pat. No. 9,351,734, filed on Apr. 26, 2013, which claims the benefit of and priority to U.S. Provisional Patent Application Ser. No. 61/661,464, filed on Jun. 19, 2012, the entire contents of each of which being incorporated by reference herein.

BACKGROUND

Technical Field

The present disclosure relates generally to a surgical instrument for applying surgical staples to body tissue. More particularly, the present disclosure relates to a surgical stapling instrument suitable for performing circular anastomosis and/or treatment to internal walls of hollow tissue organs.

Background of Related Art

Anastomosis is the surgical joining of separate hollow organ sections. Typically, an anastomosis procedure follows surgery in which a diseased or defective section of hollow tissue is removed and the remaining end sections are to be joined. Depending on the desired anastomosis procedure, the end sections may be joined by either circular, end-to-end, end-to-side, or side-to-side organ reconstruction methods.

In a circular anastomosis procedure, the two ends of the organ sections are joined by means of a stapling instrument which drives a circular array of staples through the end section of each organ section and simultaneously cores any tissue interior of the driven circular array of staples to free the tubular passage. Examples of instruments for performing circular anastomosis of hollow organs are described in U.S. Pat. Nos. 7,303,106; 6,053,390; 5,588,579; 5,119,983; 5,005,749; 4,646,745; 4,576,167; and 4,473,077, each of which is incorporated herein in its entirety by reference. Typically, these instruments include an elongated shaft having a handle portion at a proximal end to actuate the instrument, an anvil retainer, and a staple holding component disposed at a distal end. An anvil assembly including an anvil rod with attached anvil head is mounted to the distal end of the instrument adjacent the staple holding component. Opposed end portions of tissue of the hollow organ(s) to be stapled are clamped between the anvil head and the staple holding component, via the anvil retainer. Typically, a first actuation mechanism is used to approximate the anvil head and the staple holding component to clamp the tissue. The clamped tissue is stapled by driving one or more staples from the staple holding component so that the ends of the staples pass through the tissue and are deformed by the anvil head. Typically, a second actuation mechanism is used to fire the staples. It is also common for an annular knife to be concurrently advanced to core tissue within the hollow organ to free a tubular passage within the organ.

Upon engaging the first actuation mechanism and approximating the anvil head and staple holding component, the anvil rod must pass through the aperture made in the tissue where the anvil retainer passed through. The problem typically arises that the aperture diameter made by the anvil retainer is too small for the anvil rod to pass through. As a result, excess tissue is pulled into the device when approximating the anvil head. Furthermore, the tissue in some procedures is tied to the trocar by a suture. The suture can fail to slide over the anvil during retraction, also leading to too much tissue being pulled into the device. Accordingly, a need exists for a device to prevent the excessive build up of tissue which is pulled into the device, specifically, a device for enabling the anvil head to pass through the aperture made by the anvil retainer.

SUMMARY

The present disclosure relates to an anvil receiving apparatus including an anvil retainer coupled to a surgical device, and a tube surrounding a portion of the anvil retainer. The anvil retainer may include a distal annular protrusion for releasably engaging a center rod of an anvil assembly. The tube may have an outer diameter larger than the outer diameter of the center rod. Alternatively, the tube may have an outer diameter equal to the outer diameter of the center rod. The tube may include a distal tube and a proximal tube where the distal tube and proximal tubes are separated by a resilient member. The anvil retainer may further include a proximal protrusion to disable proximal movement of the proximal tube. Additionally, proximal advancement of the center rod onto the anvil retainer may cause proximal advancement of the distal tube toward the proximal tube. The anvil assembly may also include resilient arms with internal shoulders that releasably engage a distal annular protrusion of the anvil retainer.

The present disclosure also relates to a surgical stapling device including a handle assembly, a body portion extending distally from the handle assembly, and a head portion including an anvil retainer and a shell assembly. The anvil retainer may be movable in relation to the shell assembly between unapproximated and approximated positions. The anvil retainer may further include a tube surrounding a portion of the anvil retainer. The anvil retainer may include a distal annular protrusion for releasably engaging a center rod of an anvil assembly. The tube may have an outer diameter larger than the outer diameter of the center rod. Alternatively, the tube may have an outer diameter equal to the outer diameter of the center rod. The tube may include a distal tube and a proximal tube where the distal tube and proximal tubes are separated by a resilient member. The anvil retainer may further include a proximal protrusion to disable proximal movement of the proximal tube. Additionally, proximal advancement of the center rod onto the anvil retainer may cause proximal advancement of the distal tube toward the proximal tube. The anvil assembly may also include resilient arms with internal shoulders that releasably engage a distal annular protrusion of the anvil retainer.

DESCRIPTION OF THE DRAWINGS

Various embodiments of the presently disclosed surgical stapling instrument are disclosed herein with reference to the drawings, wherein:

FIG. 15B is a side view of the anvil retainer of FIG. 15A subsequent to being engaged to anvil assembly in accordance with an embodiment of the present disclosure;

FIG. 16B is a view of the anvil retainer of FIG. 16A subsequent to anvil assembly and anvil retainer passing through tissue walls;

DETAILED DESCRIPTION

Figure 1:
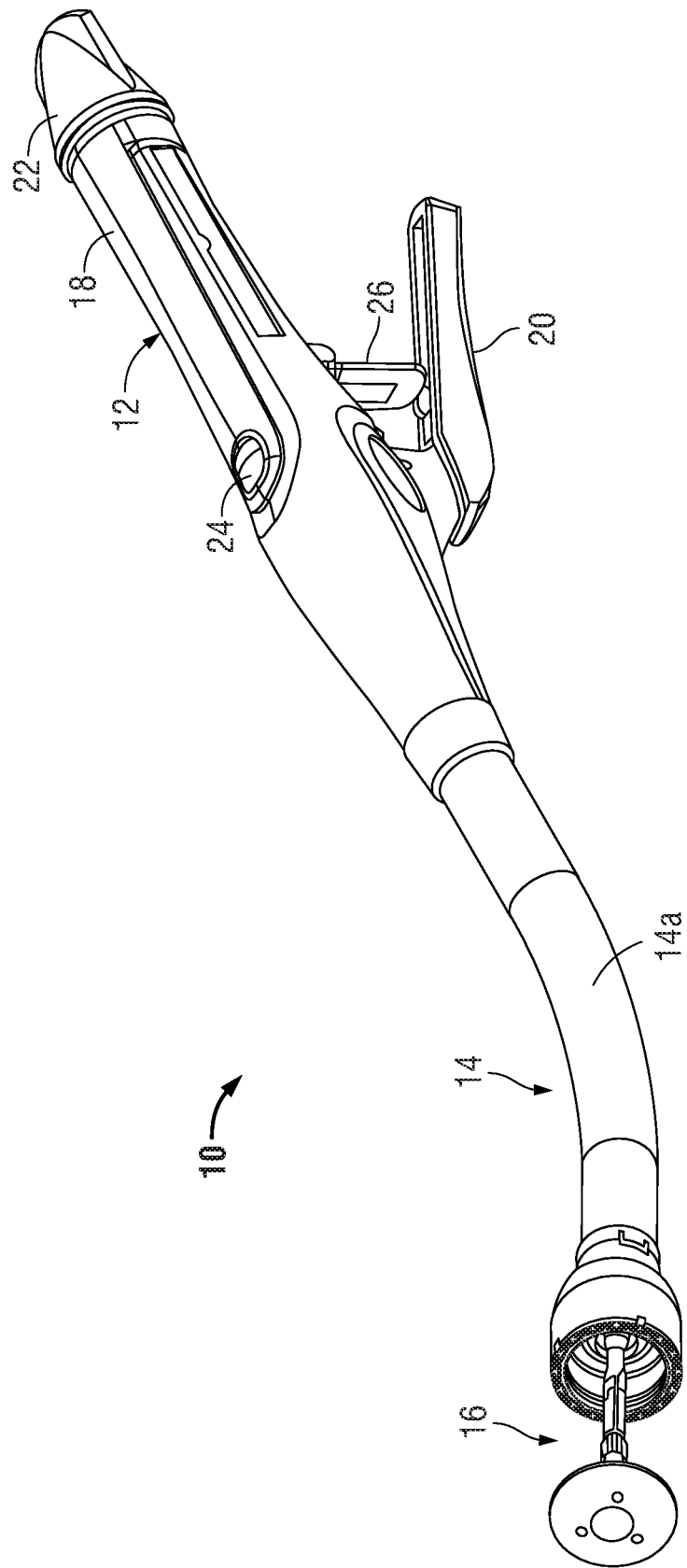
FIG. 1 is a perspective view from the distal end of the presently disclosed surgical stapling instrument illustrated in an unapproximated position, in accordance with an embodiment of the present disclosure.

Embodiments of the presently disclosed surgical stapling instrument will now be described in detail with reference to the drawings in which like reference numerals designate identical or corresponding elements in each of the several views.

Throughout this description, the term "proximal" will refer to the portion of the instrument closest to the operator and the term "distal" will refer to the portion of the instrument furthest from the operator.

Figure 2:
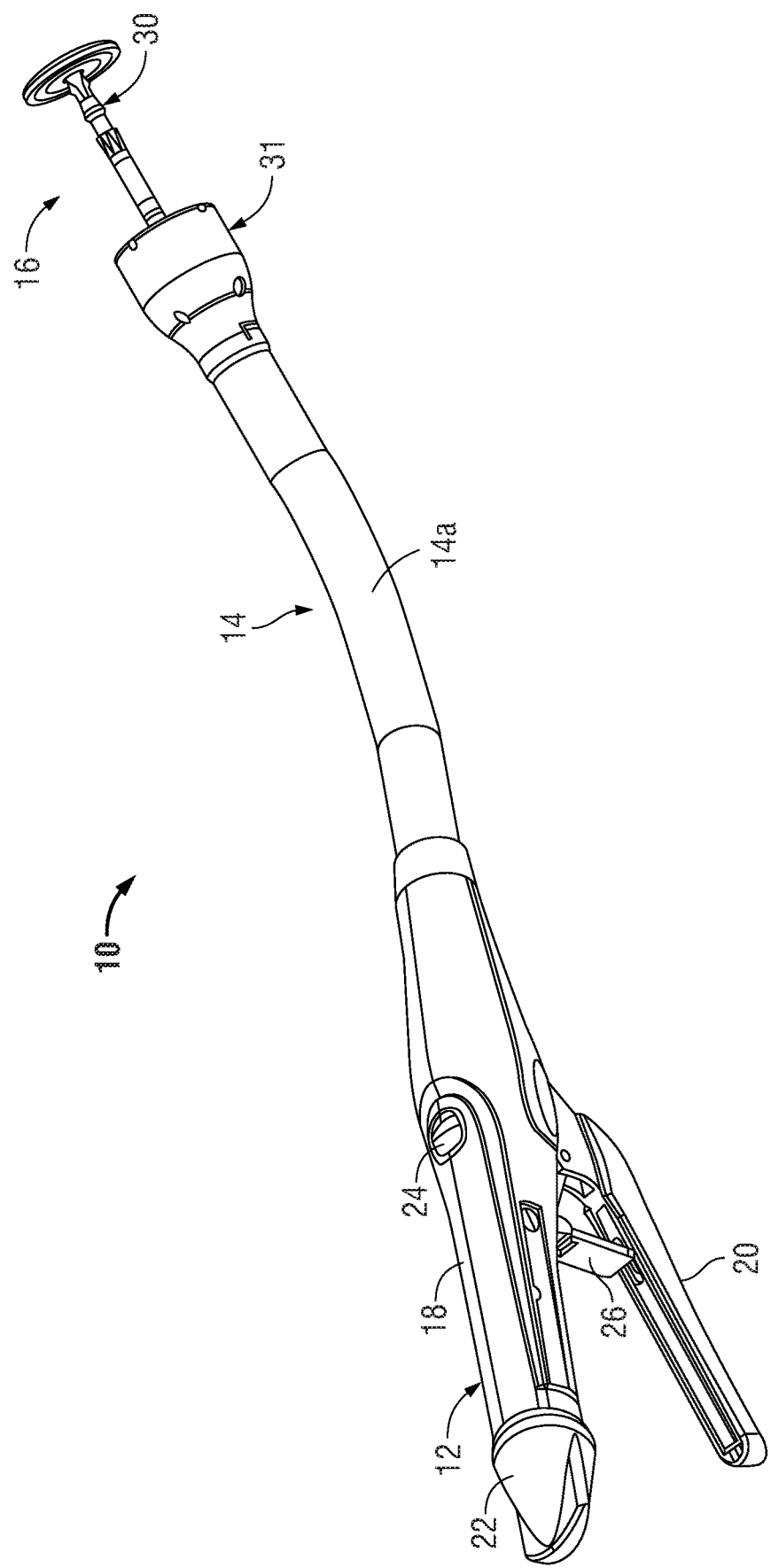
FIG. 2 is a perspective view from the proximal end of the surgical stapling device shown in FIG. 1.

FIGS. 1 and 2 illustrate one preferred embodiment of the presently disclosed surgical stapling device shown generally as 10. Briefly, surgical stapling device 10 includes a proximal handle assembly 12, an elongated central body portion 14 including a curved elongated outer tube 14a, and a distal head portion 16. Additionally or alternatively, in some surgical procedures, e.g., the treatment of hemorrhoids, it is desirable to have a substantially straight, preferably shortened, central body portion. The length, shape and/or the diameter of body portion 14 and head portion 16 may also be varied to suit a particular surgical procedure. The body portion may be flexible, or may have a flexible or articulating portion.

Handle assembly 12 includes a stationary handle 18, a firing trigger 20, a rotatable approximation knob 22 and an indicator 24. Stationary handle 18 is preferably formed from thermoplastic handle sections 18a and 18b, e.g., polycarbonate, (FIG. 5) which together define a housing for the internal components of handle assembly 12. Handle sections 18a and 18b are preferably secured together by sonic welding. Additionally or alternatively, other known securement techniques may be employed including screws, adhesives, snap-fit connectors, etc. The internal components of handle portion 12 will be discussed in detail below. Preferably, cushioned and/or resilient slip resistant portions such as a grip (not shown) can be fastened to or included as part of handle sections 18a and 18b and firing trigger 20. The slip resistant grip may be formed over handle sections 18a and 18b and firing trigger 20 using an overmolding procedure and may be formed from neoprene or rubber.

Additionally or alternatively, other suitable materials, e.g., elastomeric materials, and joining techniques may be employed. A pivotally mounted trigger lock 26 is fastened to handle assembly 12 and is manually positioned to prevent inadvertent firing of surgical stapling device 10. Indicator 24 is positioned on the stationary handle 18 and includes indicia, e.g., color coding, alphanumeric labeling, etc., to identify to a surgeon whether the device is approximated and is ready to be fired. Indicator 24 preferably has a bulbous or convex shape which extends outwardly from a top surface of handle sections 18a and 18b and is easily viewable by a surgeon from the top and sides of the stapling device.

Head portion 16 includes an anvil assembly 30 and a shell assembly 31. Each of these assemblies will be discussed in detail below. Except where otherwise noted, the components of surgical device 10 are generally formed from thermoplastics including polycarbonates, and metals including stainless steel and aluminum. The particular material selected to form a particular component will depend upon the strength requirements of the particular component. For example, the anvil is preferably formed from a metal, such as stainless steel, and the stationary handle is preferably formed from a thermoplastic such as polycarbonate. Additionally or alternatively, other materials not listed above, which preferably can withstand sterilization procedures, may be used to form components of surgical stapling device 10 provided the materials are suitable for surgical use and meet the strength requirements of the particular component.

Figure 3A:
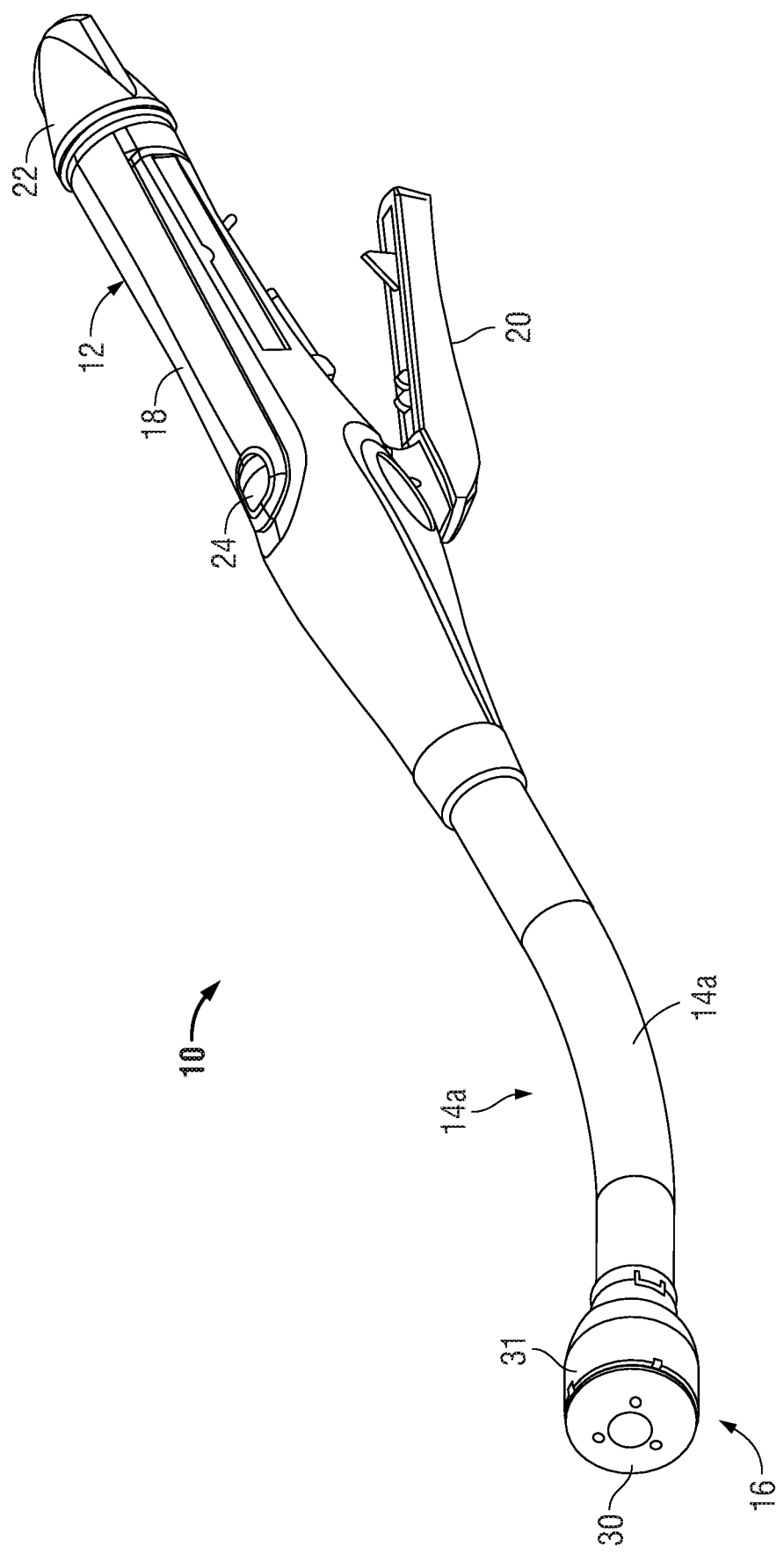
FIG. 3A is a perspective view of the surgical stapling instrument of FIG. 1 illustrated in an approximated position.
Figure 3B:
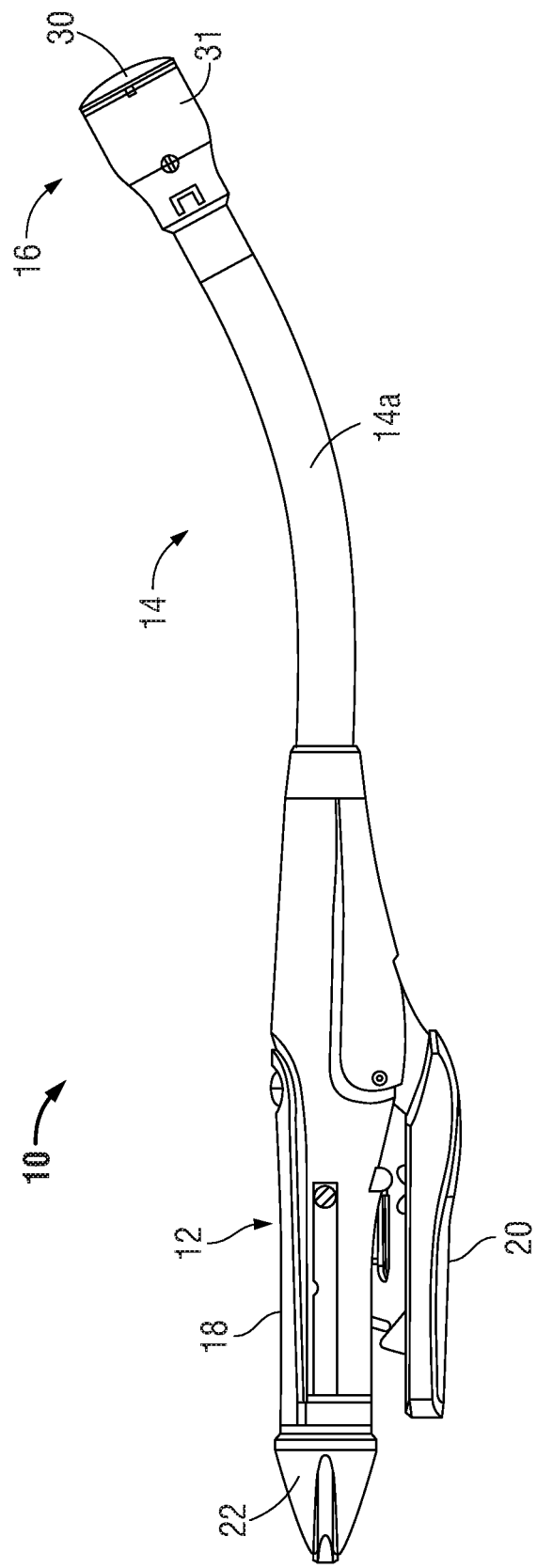
FIG. 3B is a side view of the surgical stapling instrument of FIG. 1 illustrated in a fired position.

Turning now to FIGS. 3A and 3B, in operation, rotation of approximation knob 22 causes movement of anvil assembly 30 in relation to shell assembly 31 between spaced (FIGS. 1 and 2) and approximated (FIGS. 3A and 3B) positions, as approximation knob 22 is mechanically engaged with anvil retainer 38 (FIG. 7), which is fastened to anvil assembly 30. It is envisioned that rotation of approximation knob 22 in a first direction (e.g., clockwise) causes proximal movement of anvil assembly 30 (i.e., towards its approximated position), and rotation of approximation mechanism 22 in a second opposite direction (e.g., counter-clockwise) causes distal movement of anvil assembly 30 (i.e., towards its spaced position) when anvil assembly 30 is attached to anvil retainer 38. Details of the approximation mechanism are disclosed for example in U.S. Pat. No. 7,303,106, the entire contents of which are incorporated herein by reference.

Actuation of firing trigger 20 towards stationary handle 18, causes staples to be ejected from shell assembly 31 towards anvil assembly 30. That is, firing trigger 20 is disposed in mechanical cooperation with a pusher (FIG. 7), such that actuation of firing trigger 20 causes advancement of the pusher into contact with the staples, which ejects into staple deforming pockets of anvil assembly 30. Details of the firing are disclosed for example in U.S. Pat. No. 7,303,106, the entire contents of which are incorporated herein by reference.

Figure 4A:
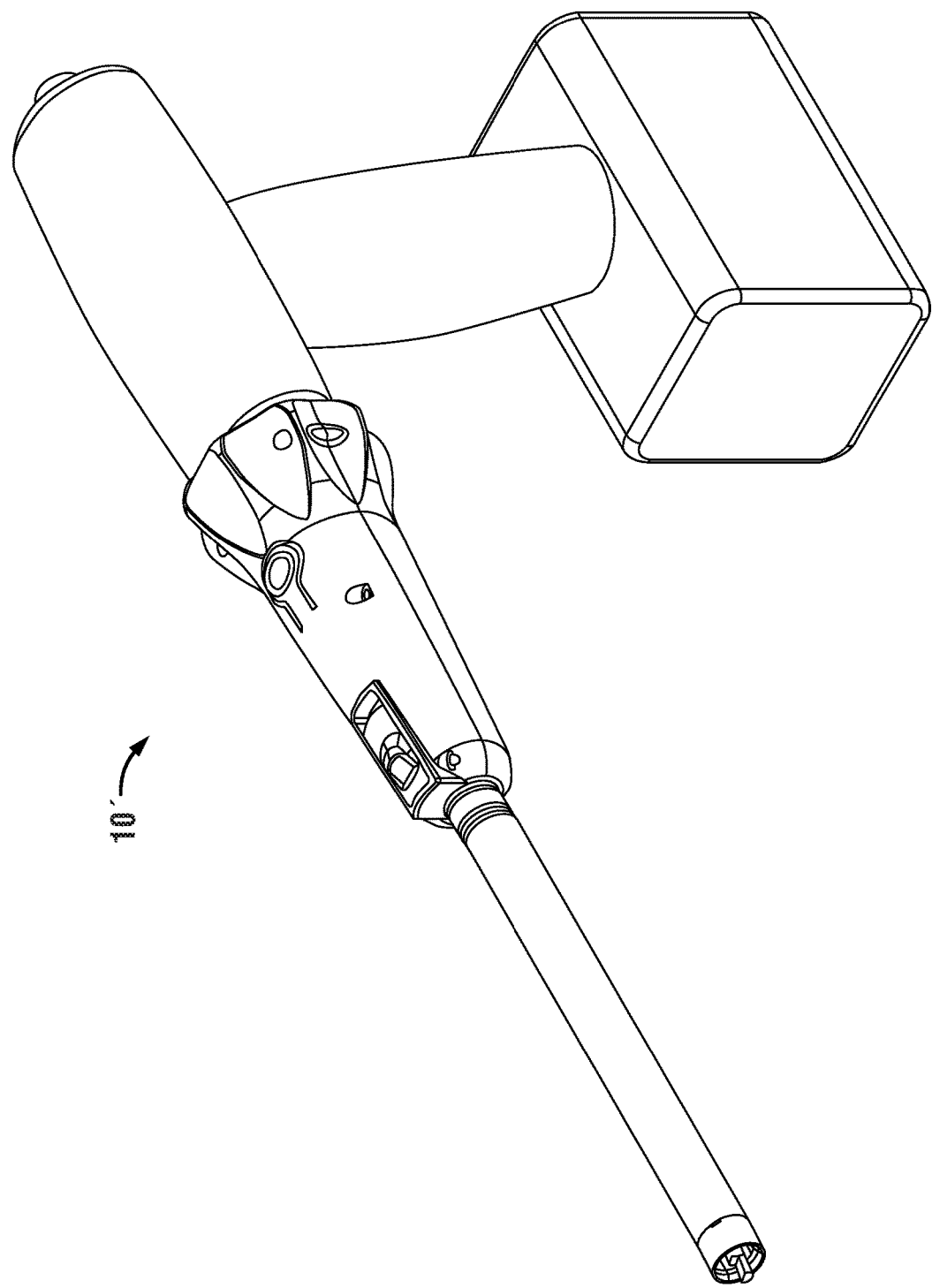
FIG. 4A is a perspective view of another embodiment of a surgical stapling instrument in accordance with another embodiment of the present disclosure.
Figure 4B:
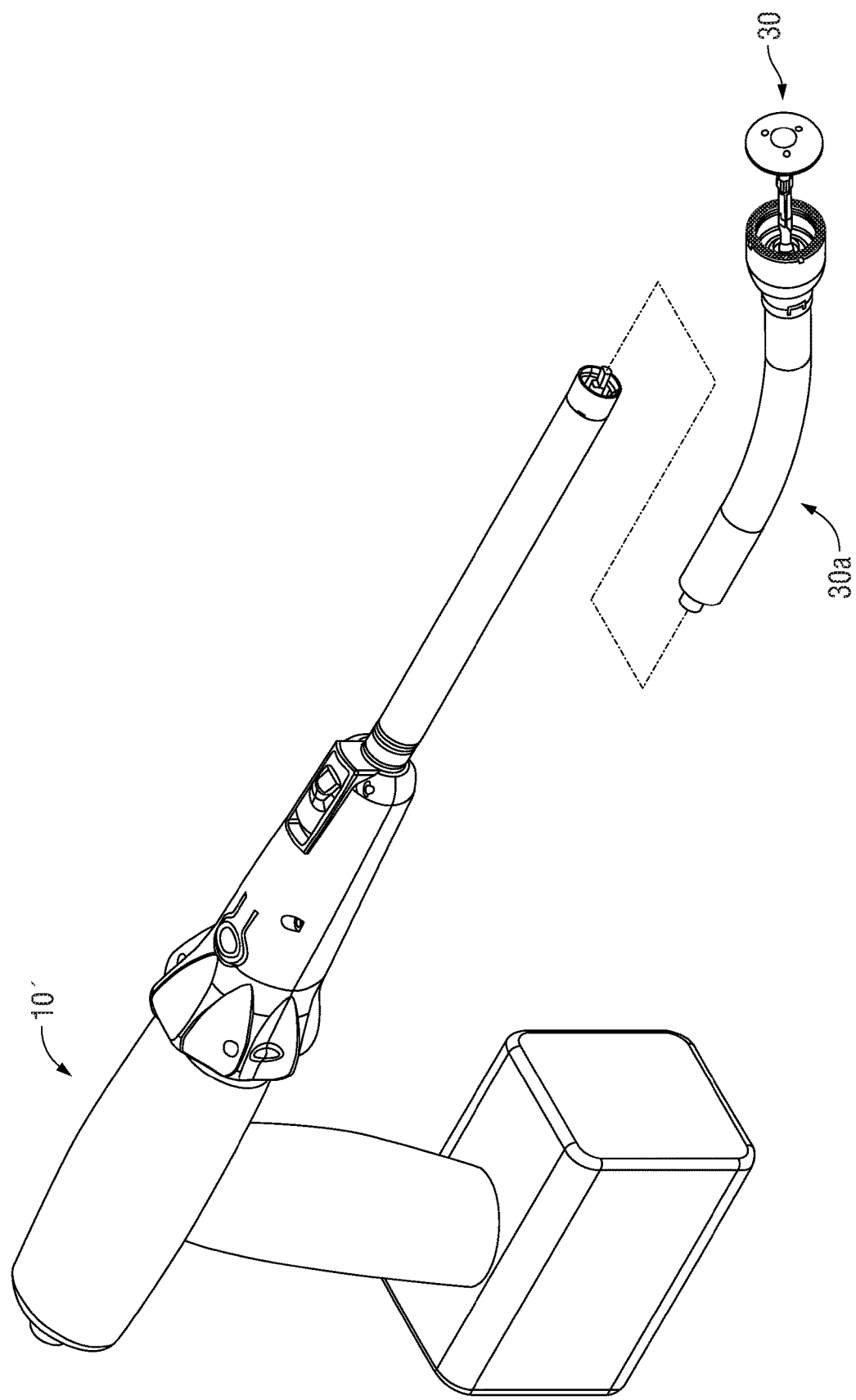
FIG. 4B is a perspective view of the surgical stapling device of FIG. 4A with the attachment removed.

With additional reference to FIGS. 4A and 4B, it is also contemplated that, in certain embodiments, the apparatus has a replaceable head 30a including the cartridge assembly, anvil member 30 and associated mechanisms. The stapling device can include the manual stapling device 10 of FIG. 1 and as described herein, or can include a powered stapling device 10' having first and second drive members as shown in FIGS. 4A and 4B. For example, U.S. patent application Ser. No. 12/946,082, filed Nov. 15, 2010 (now U.S. Pat. No. 8,806,973), the entire disclosure of which is hereby incorporated by reference herein, discloses a surgical device (shown as surgical stapling device 10' in FIGS. 4A and 4B herein) having a powered actuator assembly. Such actuator assembly can be powered by a motorized handle. The drive members, in some embodiments, are rotatable drive shafts that advance the pusher member to fire staples, advance a knife to cut tissue, and retract the anvil retainer to clamp tissue. It is also contemplated that the stapling device 10' can be configured to apply two or three rows of staples, and that the staples can have a curved or bent backspan, in any of the embodiments disclosed herein. In any of the disclosed embodiments, the staples in the shell assembly can be all the same sizes, or the sizes can vary. For example, it is contemplated that the staples in a row of staples can have a different size from the staples in another row. The spring loaded anvil retainer 38 of the present disclosure may be used with both surgical stapling devices 10, 10'. However, for the sake of simplicity, the anvil retainer 38 will be described in use with stapling device 10, and it is noted that its use with stapling device 10' is substantially similar.

Figure 5:
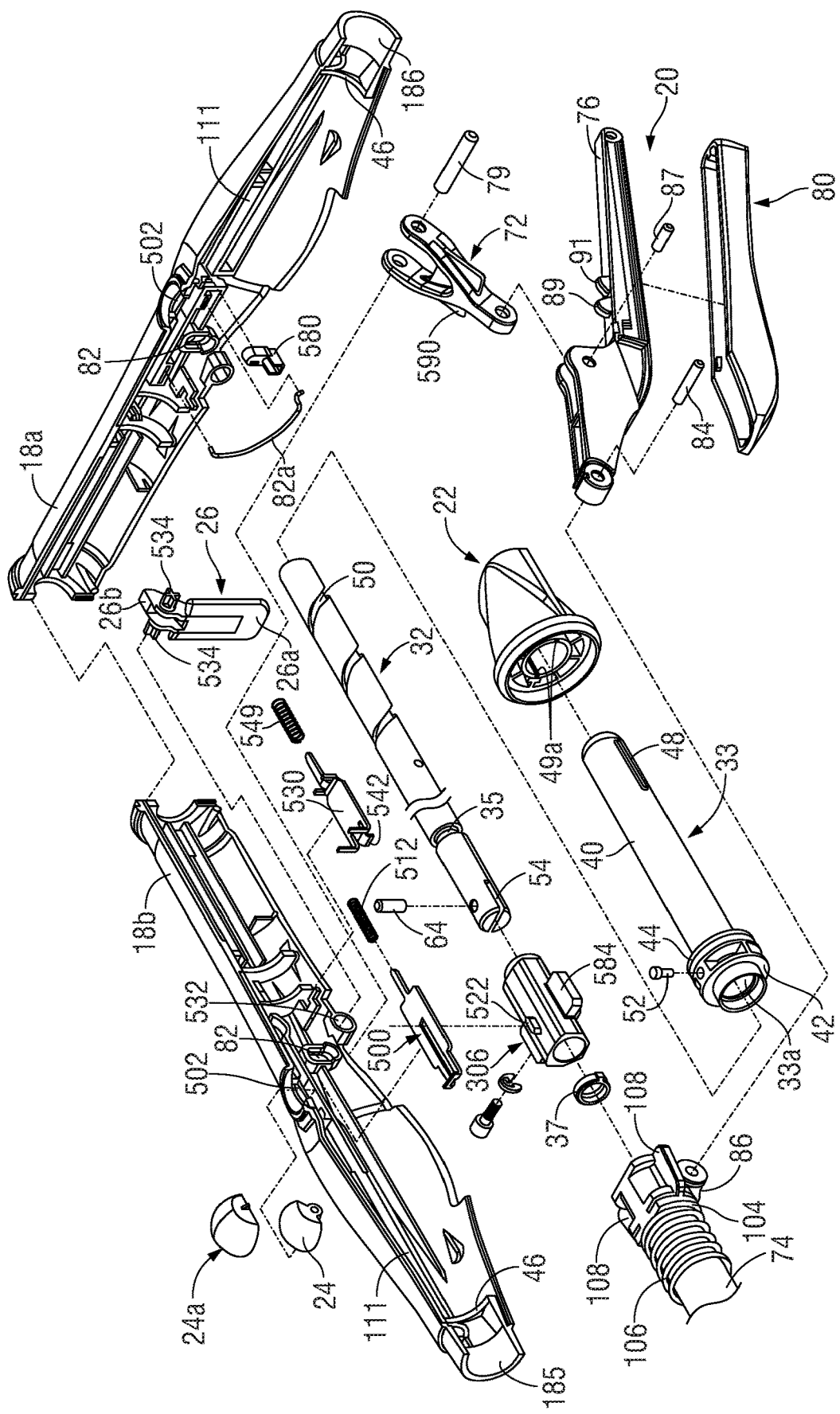
FIG. 5 is an exploded view of the handle assembly, with parts separated, of the surgical stapling device of FIG. 1.
Figure 6:
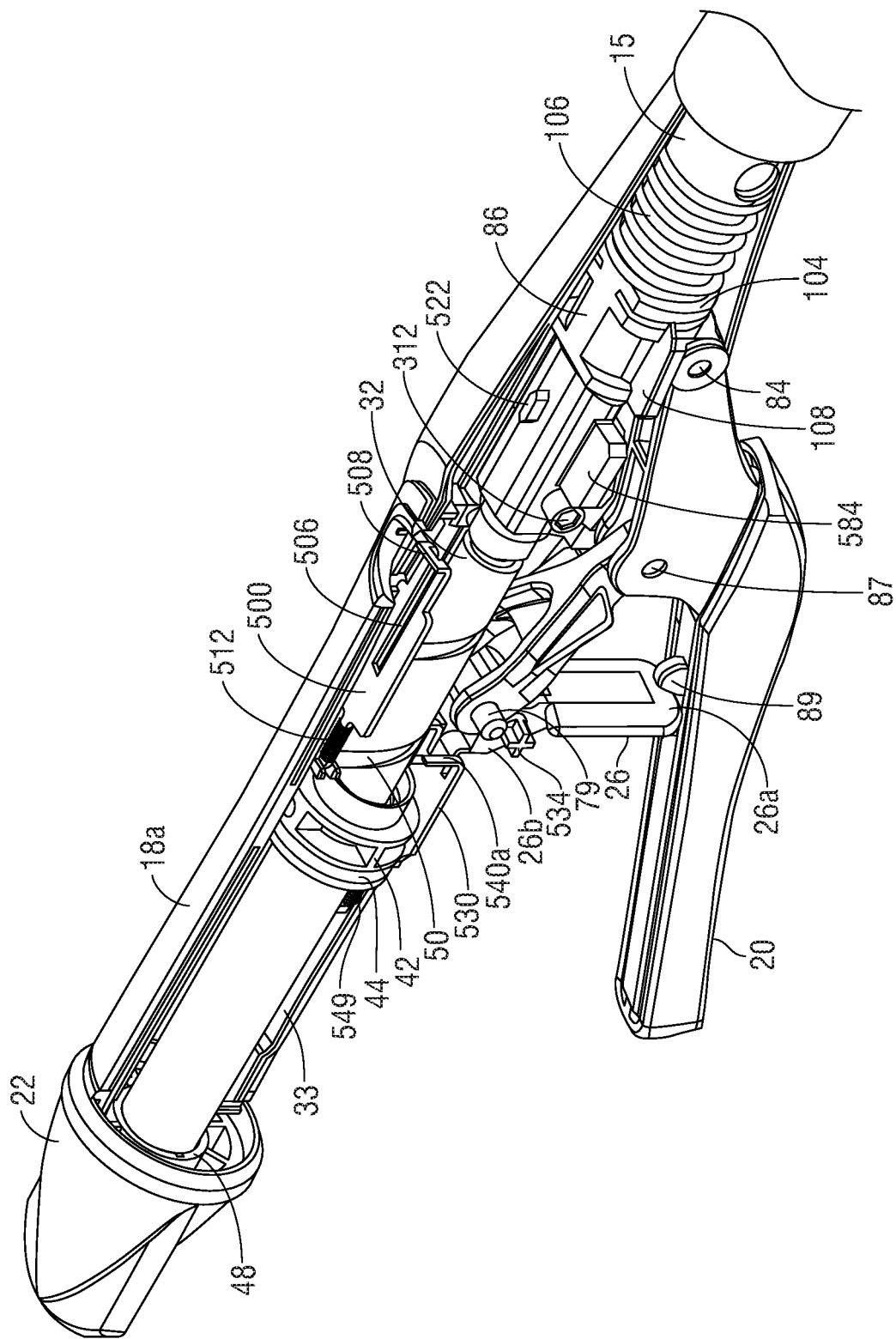
FIG. 6 is a side perspective view of the handle assembly of the surgical stapling device as shown in FIG. 1 with a handle section removed.
Figure 7:
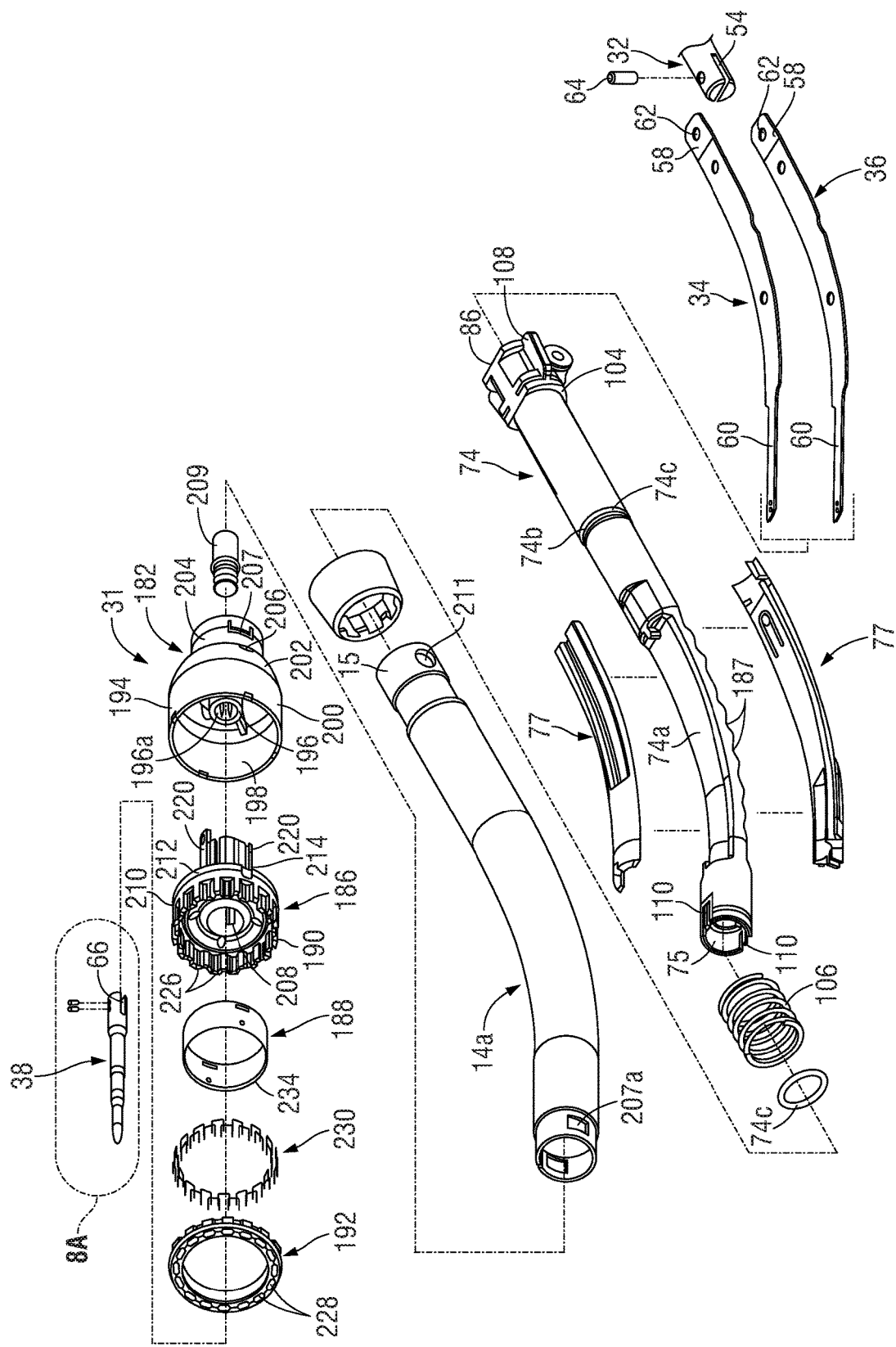
FIG. 7 is an exploded view, with parts separated, of the central body portion and distal head portion of the surgical stapling device shown in FIG. 1.
Figure 8A:
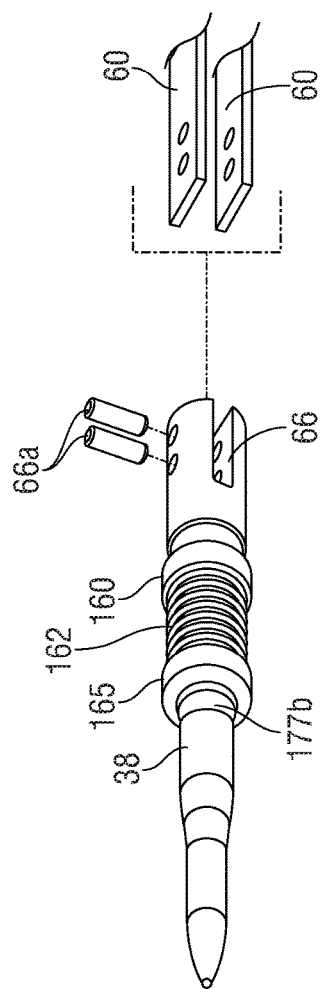
FIG. 8A is an enlarged view of the area of detail of FIG. 7.
Figure 8B:
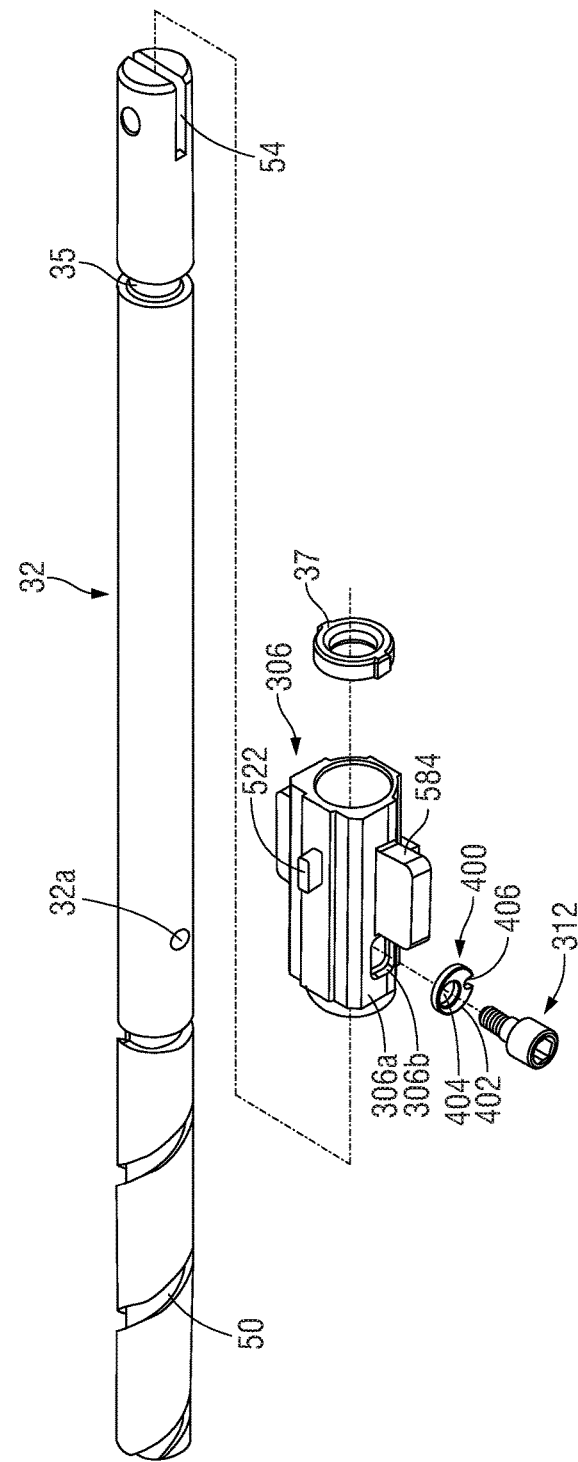
FIG. 8B is an enlarged side perspective view of the anvil retainer and band body portions of the central body portion and the screw and screw stop of the approximation mechanism of the surgical stapling device shown in FIG. 1.

FIGS. 5-6 illustrate the internal components of handle assembly 12. The internal components include the proximal components of approximation and firing mechanisms, a firing lockout mechanism and an indicator drive mechanism. FIGS. 7 and 8A illustrate the internal components of elongated body portion 14. These components include the distal components of the approximation and firing mechanisms. Each of these mechanisms will be disclosed in detail hereinbelow.

Referring to FIGS. 5-8A and 8B, the approximation mechanism includes approximation knob 22, a drive screw 32, a rotatable sleeve 33, first and second screw extensions 34 and 36 (FIG. 7), respectively, and an anvil retainer 38. Rotatable sleeve 33 includes a substantially cylindrical hollow body portion 40 and a substantially cylindrical collar 42 which together define a central bore 33a. Collar 42 has an annular groove 44 formed thereabout which is dimensioned to receive an inwardly extending flange 46 formed on an inner wall of handle sections 18a and 18b. Engagement between groove 44 and flanges 46 axially fixes sleeve 33 within handle 18 while permitting rotation of sleeve 33 in relation to stationary handle 18. The proximal end of body portion 40 of rotatable sleeve 33 extends through an opening 186 in the proximal end of stationary handle 18. A pair of diametrically opposed elongated ribs 48 are positioned or formed on the outer surface of body portion 40. Approximation knob 22 includes a pair of internal slots 49a positioned to receive ribs 48 of sleeve 33 to rotatably fix sleeve 33 to knob 22, such that rotation of knob 22 causes concurrent rotation of sleeve 33.

The proximal half of screw 32 includes a helical channel 50 and is dimensioned to be slidably positioned within central bore 33a of rotatable sleeve 33. The distal end of screw 32 includes an annular recess 35 dimensioned to receive a seal member 37 (FIG. 5) for providing a fluid tight seal between the outer surface of screw 32 and the inner surface of pusher link 74. A pin 52 (FIG. 5) extends radially through cylindrical collar 42 of sleeve 33 into helical channel 50. Since sleeve 33 is axially fixed with respect to stationary handle 18, rotation of sleeve 33 about screw 32 causes pin 52 to move along channel 50 of screw 32 to effect axial movement of screw 32 within stationary handle 18.

Referring to FIGS. 7-8A and 8B, the distal end of screw 32 includes a transverse slot 54. Top and bottom screw extensions 34 and 36 (FIG. 7) each include a proximally located flexible flat band portion 58 and a distally located flat band portion 60. Alternately, it is envisioned that screw extensions 34 and 36 may have other than a band configuration. For example, screw extensions 34 and 36 may be semi-circular or circular in cross-section. The flexibility of top and bottom screw extensions 34 and 36 permits movement of screw extensions 34 and 36 through curved elongated body portion 14. The proximal end of each band portion 58, 60 includes a hole 62 dimensioned to receive a pin 64 for securing the proximal end of screw extensions 34 and 36 within transverse slot 54 of screw 32. Alternately, other fastening techniques may be used to secure each band portion 58 to screw 32, e.g., welding, crimping, etc. Distally located band portion 60 of each screw extension 34 and 36 is dimensioned to be received within a transverse slot 66 formed in a proximal end of anvil retainer 38 (FIG. 8A) to fasten anvil retainer 38 to the distal end of screw extensions 34 and 36. Preferably, a pair of pins 66a which extend through the proximal end of anvil retainer 38 and band portions 60 are used to secure screw extensions 34 and 36 to anvil retainer 38. Additionally or alternatively, band portions 60 can be brazed or welded within slot 66 or other fastening techniques may be used to secure band portions 60 of screw extensions 34 and 36 to anvil retainer 38, e.g., screws, crimping, etc. Anvil retainer 38 includes a distal annular protrusion 177b (FIG. 8A) which is configured to engage the anvil assembly 30 (FIG. 1) in a manner to be discussed in detail below. Additionally or alternatively, distal protrusion 177b need not be annular or may include different attachment structure, e.g., recesses, grooves, etc.

Referring again to FIGS. 5-8A and 8B, when approximation knob 22 is manually rotated, rotatable sleeve 33 is rotated about the proximal end of screw 32 to move pin 52 along helical channel 50 of screw 32. Since sleeve 33 is axially fixed to stationary handle 18, as pin 52 is moved through channel 50, screw 32 is advanced or retracted within stationary handle 18. As a result, top and bottom screw extensions 34 and 36, which are fastened to the distal end of screw 32, and anvil retainer 38, which is fastened to the distal end of screw extensions 34 and 36, are moved axially within elongated body portion 14. Since anvil assembly 30 is secured to the distal end of anvil retainer 38, rotation of approximation knob 22 will effect movement of anvil assembly 30 in relation to shell assembly 31 between spaced and approximated positions.

Referring to FIGS. 5-7, the firing mechanism includes firing trigger 20, a firing link 72 and an elongated pusher link 74 (FIG. 7). Firing trigger 20 includes a body portion 76 and a trigger cover 80. A cushioned gripping surface (not shown) preferably formed of neoprene or rubber is provided on trigger cover 80. The cushioned gripping surface provides a non-slip cushioned surface to make actuation of surgical stapling device 10 more comfortable to a surgeon. The distal end of body portion 76 of trigger 20 is pivotally connected to a coupling member 86 by a pivot member 84. Coupling member 86 is secured to the proximal end of pusher link 74 and may be formed integrally with pusher link 74 or as a separate element fastened thereto. Firing link 72 has a distal end pivotally secured to body portion 76 of trigger 20 by a pivot member 87 and a second end pivotally secured within a vertical slot 82 formed between stationary handle half-sections 18a and 18b of stationary handle 18 by pivot member 79. Pivot member 79 is free to move vertically within slot 82. A spring (not shown) is supported within handle 18 to urge pivot member 79 downwardly towards the bottom of slot 82. Body portion 76 of trigger 20 further includes a pair of abutments including an abutment 89 and an abutment 91 which are positioned to engage the distal end 26a (FIG. 6) of trigger lock 26 in a manner to be described in greater detail below to prevent actuation of trigger 20 prior to approximation of surgical stapling device 10.

Coupling member 86 which is supported on the proximal end of elongated pusher link 74 includes a flange 104 (FIG. 7). A spring 106 is positioned between a proximal end of outer tube 14a and flange 104 (FIG. 6) to bias pusher link 74 proximally to a retracted, non-fired position. A pair of wings 108 extends radially outwardly from coupling member 86. Wings 108 are dimensioned to slide along channels 111 (FIG. 5) formed along the internal walls of stationary handle 18 to maintain proper alignment of pusher link 74 within stationary handle 18 during firing of device 10.

Referring to FIG. 7, the distal end of pusher link 74 includes a pair of engagement fingers 110 which are dimensioned to lockingly engage with members 220 formed in the proximal end of pusher back 186. Pusher back 186 forms part of shell assembly 31 and will be discussed in greater detail below. Pusher link 74 is preferably formed from a flexible plastic material and includes a plurality of notches 187 which allow the pusher link to bend more easily as it moves through body 14. Pusher link 74 defines a hollow channel 75 for slidably receiving the approximation mechanism. A flat surface or cutout 74a (FIG. 7) formed in pusher link 74 slidably supports screw extensions 34 and 36 which are positioned in juxtaposed alignment. Spacers 77 are positioned within outer tube 14a adjacent cutout 74a to provide additional support for screw extensions 34 and 36 and pusher link 74 to prevent each component from buckling during actuation. An annular channel 74b is formed about pusher link 74 to receive an O-ring seal 74c. Pusher link 74 is slidably positioned within body portion 14 such that O-ring 74c seals the space between pusher link 74 and an internal wall of outer tube 14a. Operation of the firing mechanism of the device will be described in detail below.

Referring again to FIGS. 5-7, when firing trigger 20 is actuated, i.e., pivoted about pivot member 84, firing link 72 is moved proximally until pivot member 79 engages an abutment surface (not shown) formed on screw stop 306 (FIG. 5). Screw stop 306 is axially fixed to screw 32 in a manner to be described in detail below. Thereafter, the firing trigger 20 advances the pusher link 74 distally against the bias of spring 106. Since the distal end of pusher link 74 is connected to pusher back 186, actuation of firing trigger 20 effects advancement of pusher back 186 within shell assembly 31 to eject staples from shell assembly 31 in a manner to be described below.

Figure 9:
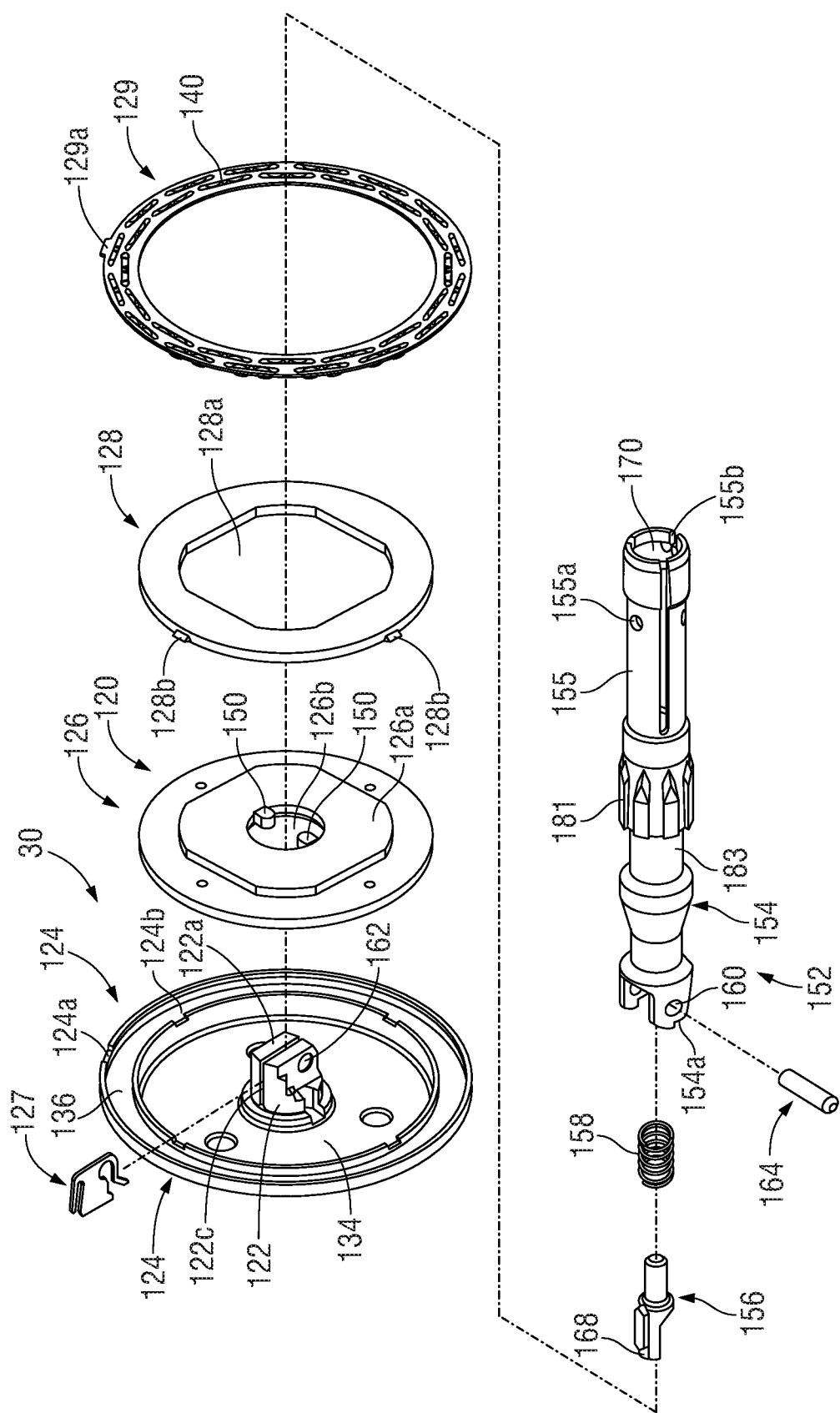
FIG. 9 is an exploded view, with parts separated, and shown in perspective from the proximal end of the anvil assembly of the surgical stapling device shown in FIG. 1.

Referring to FIG. 7, shell assembly 31 includes a shell 182, a pusher back 186, a cylindrical knife 188, and a staple guide 192. Shell 182 includes an outer housing portion 194 and an inner guide portion 196 having grooves 196a for mating with splines 181 on anvil center rod 154 (FIG. 9). Features other than splines are contemplated, and the anvil center rod may not have any protruding features. Outer housing portion 194 defines a throughbore 198 having a distal cylindrical section 200, a central conical section 202 and a proximal smaller diameter cylindrical section 204. A plurality of openings 206 are formed in conical section 202. Openings 206 are dimensioned to permit fluid and tissue passage during operation of the device. A pair of diametrically opposed flexible engagement members 207 are formed on proximal cylindrical section 204 of shell 182. Engagement members 207 are positioned to be received in openings 207a formed on the distal end of outer tube 14a to secure shell 182 to elongated body 14. A pair of openings 211 formed in the proximal end of outer tube 14a are dimensioned to receive protrusions (not shown) formed on the internal wall of stationary handle 18 to facilitate attachment of tube 14a to handle portion 12.

Pusher back 186 includes a central throughbore 208 which is slidably positioned about inner guide portion 196 of shell 182. Pusher back 186 includes a distal cylindrical section 210 which is slidably positioned within distal cylindrical section 200 of shell 182, a central conical section 212 and a proximal smaller diameter cylindrical section 214. The proximal end of pusher back 186 includes members 220 which are configured to lockingly engage with resilient fingers 110 of pusher link 74 to fasten pusher link 74 to pusher back 186 such that a distal face of pusher link 74 abuts a proximal face of pusher back 186.

The distal end of pusher back 186 includes a pusher 190. Pusher 190 includes a multiplicity of distally extending fingers 226 dimensioned to be slidably received within slots 228 formed in staple guide 192 to eject staples 230 therefrom. Cylindrical knife 188 is frictionally retained within the central throughbore of pusher back 186 to fixedly secure knife 188 in relation to pusher 190. Alternately, knife 188 may be retained within pusher back 186 using adhesives, crimping, pins, etc. The distal end of knife 188 includes a circular cutting edge 234.

In operation, when pusher link 74 is advanced distally in response to actuation of firing trigger 20, as will be described below, pusher back 186 is advanced distally within shell 182. Advancement of pusher back 186 advances fingers 226 through slots 228 of staple guide 192 to advance staples 230 positioned within slots 228 and ejects staples 230 from staple guide 192 into staple deforming pockets 140 of anvil 129. Since knife 188 is secured to pusher back 186, knife 188 is also advanced distally to core tissue as will be described in more detail below.

Continuing with reference to FIG. 7, and additionally referring to FIG. 9, a rigid bushing 209 is supported in the proximal end of inner guide portion 196 of shell 182. Bushing 209 defines a throughbore dimensioned to slidably receive anvil retainer 38 and center rod 154 of anvil assembly 30. Bushing 209 provides lateral support for flexible arms 155 of center rod 154 when the anvil assembly 30 has been approximated to prevent disengagement of anvil assembly 30 from anvil retainer 38. In the unapproximated position, flexible arms 155 of center rod 154 are positioned externally of bushing 209 to permit removal of anvil assembly 30 from retainer 38.

Operation of surgical stapling device 10 with respect to the attachment of anvil assembly 30 to anvil retainer 38 will now be described in detail with reference to FIGS. 10-16.

Figure 10:
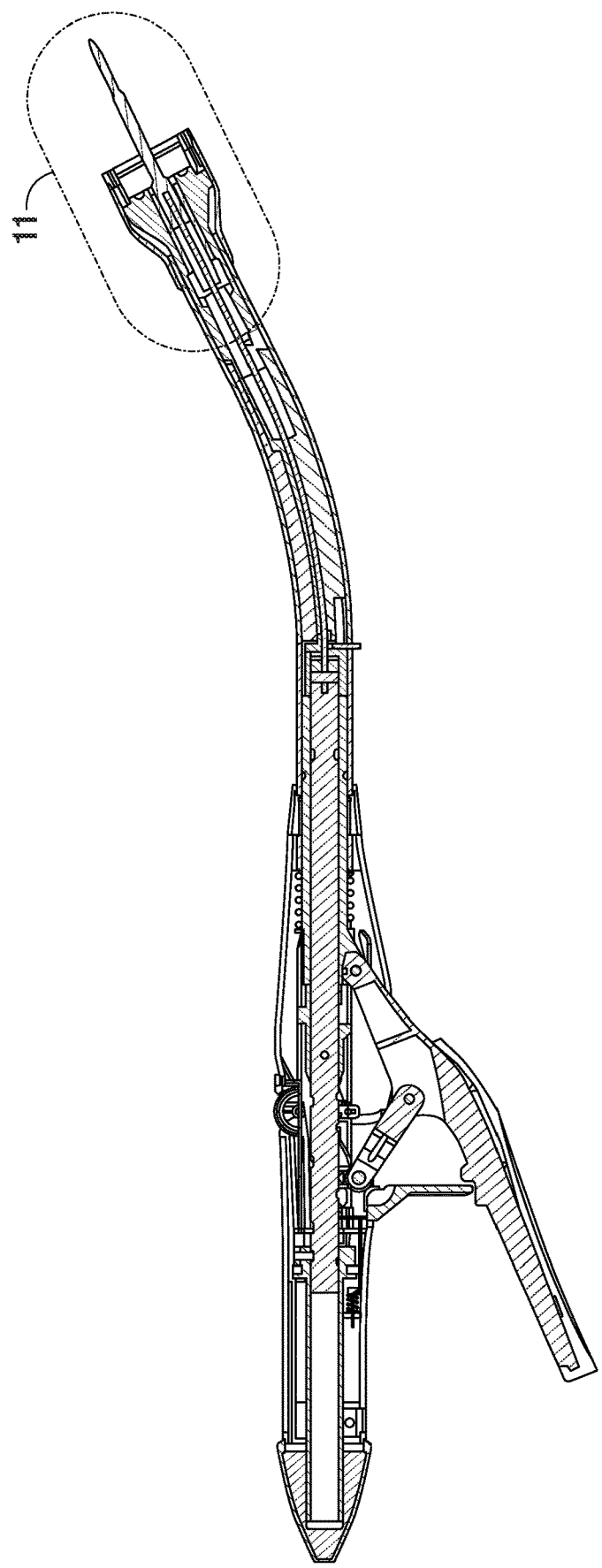
FIG. 10 is a side cross-sectional view of the surgical stapling device shown in FIG. 1 with the anvil assembly removed.
Figure 11:
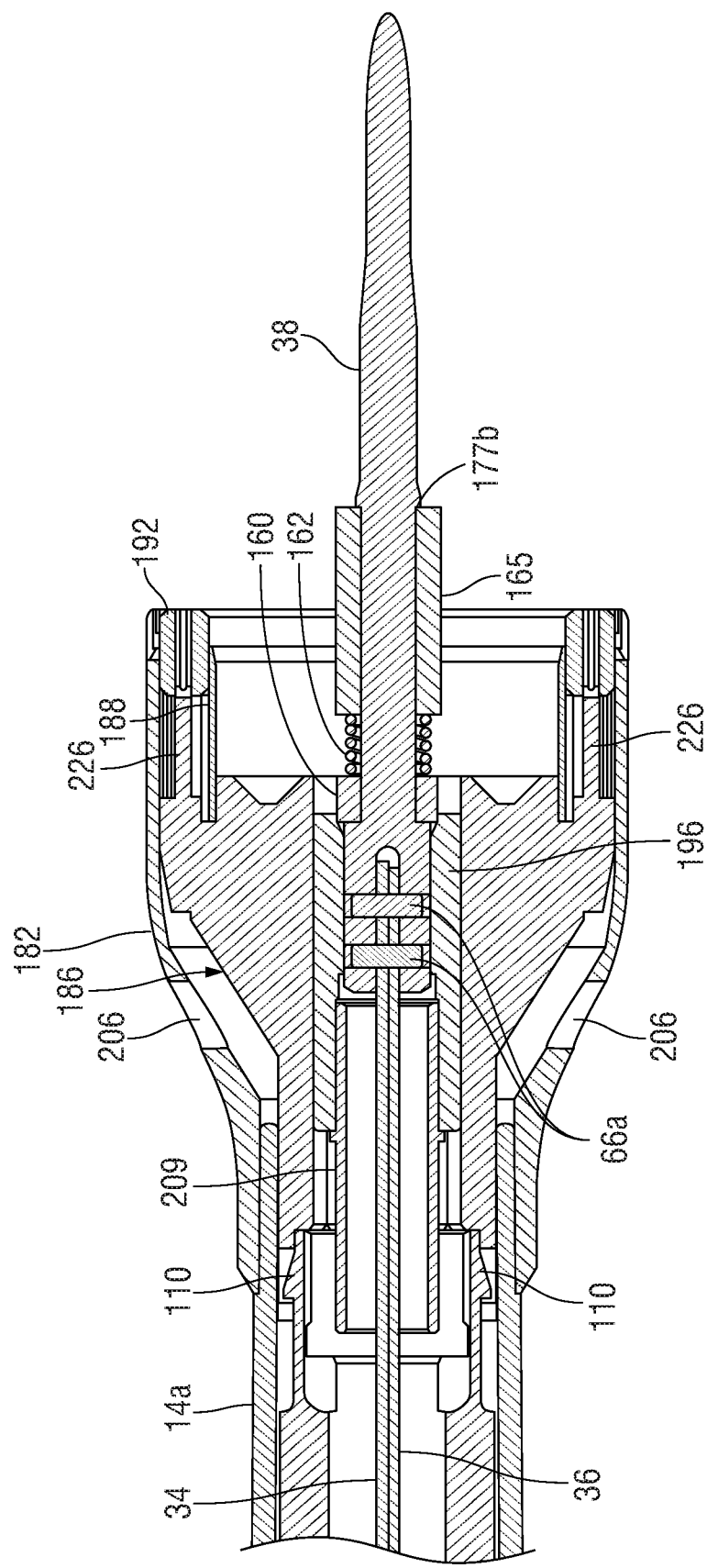
FIG. 11 is an enlarged view of the area of detail in FIG. 10.
Figure 12:
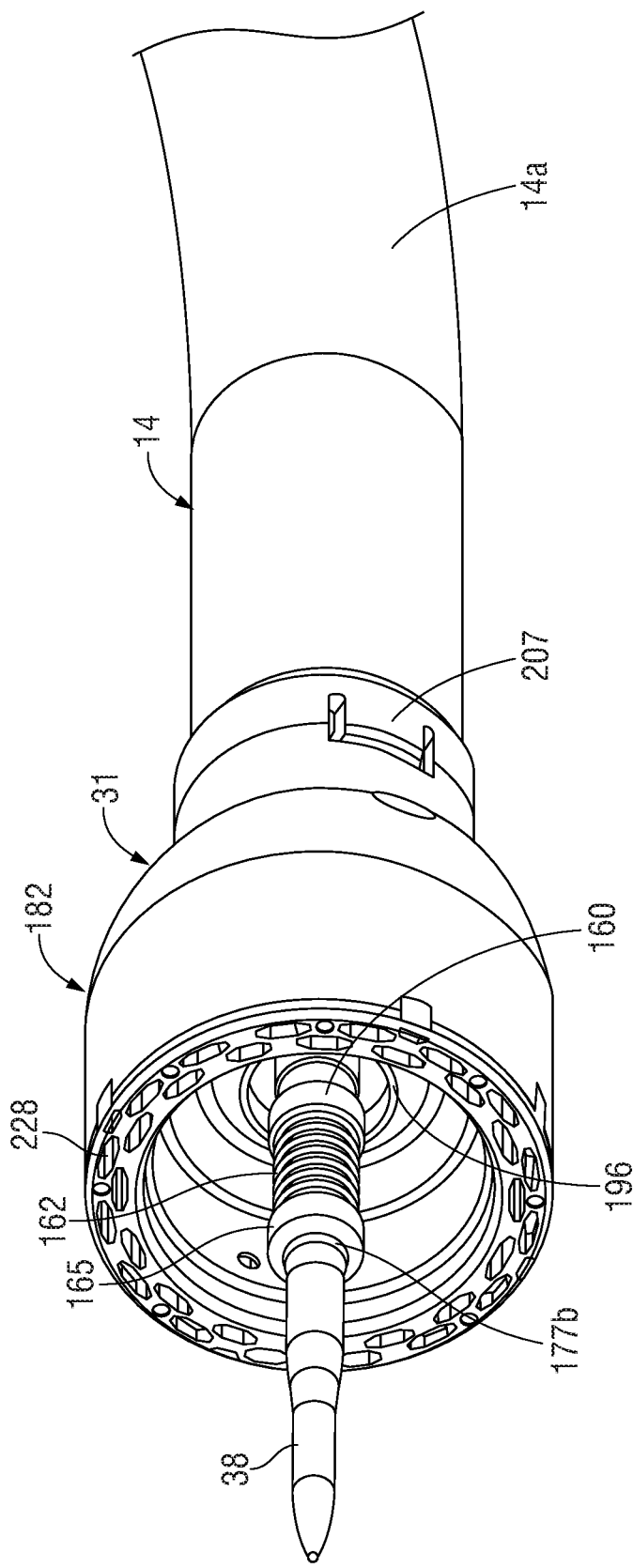
FIG. 12 is a perspective view from the front of the distal end of the surgical stapling device shown in FIG. 10 with the anvil assembly removed.

FIGS. 10-12 illustrate surgical stapling device 10 in the unapproximated or open position prior to attachment of anvil assembly 30 to anvil retainer 38. In this position, and referring back to FIG. 5, biasing member (not shown) is engaged with coupling 86 to urge pusher link 74 to its proximal-most position in which coupling 86 abuts screw-stop 306. Biasing member 512 is engaged with slide member 500 of the indicator mechanism to position slide member 500 in engagement with projection 518 of indicator 24 to pivot indicator 24 in a clockwise direction. Biasing member 549 is engaged with body 536 of lockout member 530 to urge lockout member 530 to its distal-most position, wherein lip portion 542 of lockout member 530 is positioned above extension 26b of trigger lock 26 to prevent movement of trigger lock 26 to the unlocked position. Biasing member 82a is also engaged with pivot member 79 to urge pivot member 79 to the base of vertical slot 82.

Figure 13:
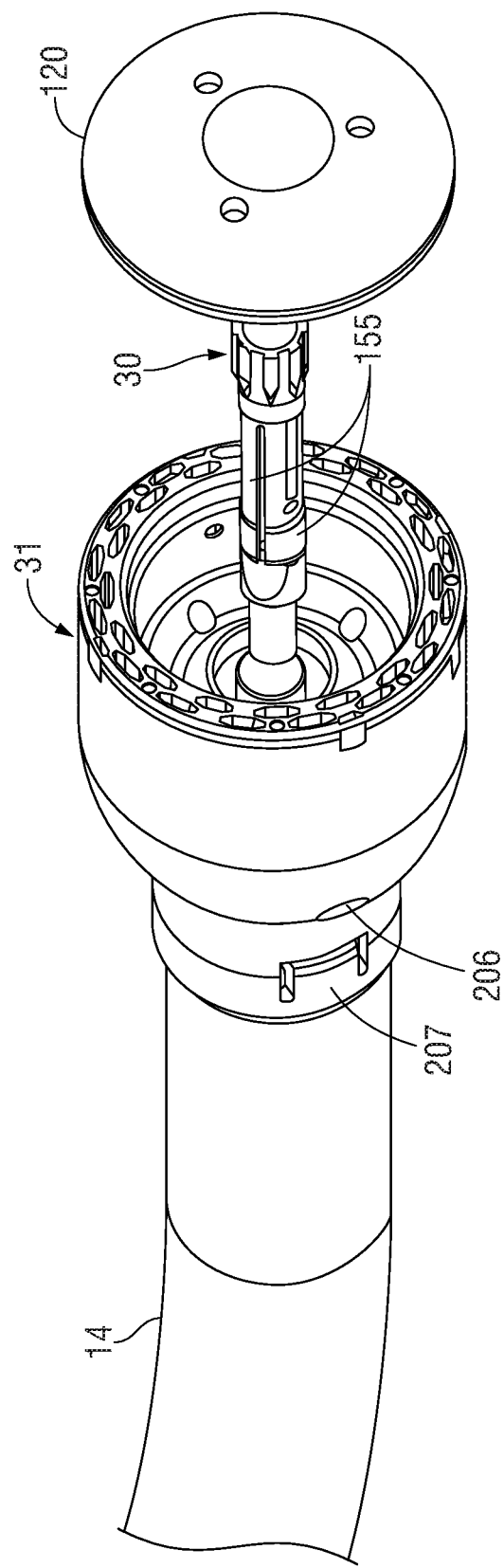
FIG. 13 is a perspective view from the front of the distal end of the surgical stapling device shown in FIG. 12 with an anvil assembly attached.
Figure 14:
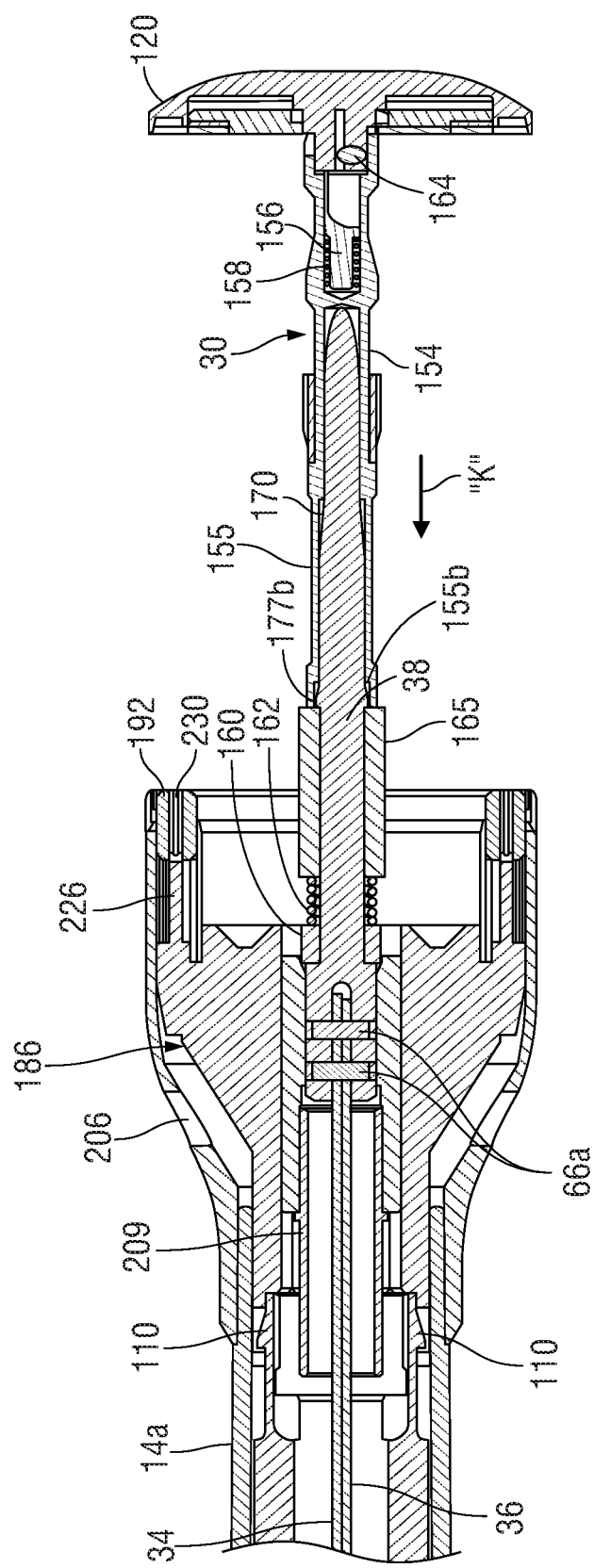
FIG. 14 is a side cross-sectional view of the distal end of the surgical stapling device shown in FIG. 13.

FIGS. 13-14 illustrate surgical stapling device 10 with anvil assembly 30 attached to anvil retainer 38 and the surgical stapling device 10 in the unapproximated or open position. Referring to FIG. 14, during attachment of anvil assembly 30 to anvil retainer 38, anvil retainer 38 is positioned within bore 170 of center rod 154 of anvil assembly 30. Flexible arms 155 of the center rod deflect outwardly to accommodate the anvil retainer 38. Center rod 154 is advanced onto anvil retainer 38 in the direction indicated by arrow "K" in FIG. 14 which pushes section 165 of the anvil retainer proximal as it compresses 162. This allows internal shoulder 155b of flexible arms 155 to pass over annular protrusion 177 formed on anvil retainer 38. At this point, flexible arms 155 releasably engage the anvil retainer 38. The position of the remaining components of stapling device 10 are not affected by attachment of anvil assembly 30 to anvil retainer 38 and remain as described above and shown in FIG. 10-12.

Figure 15A:
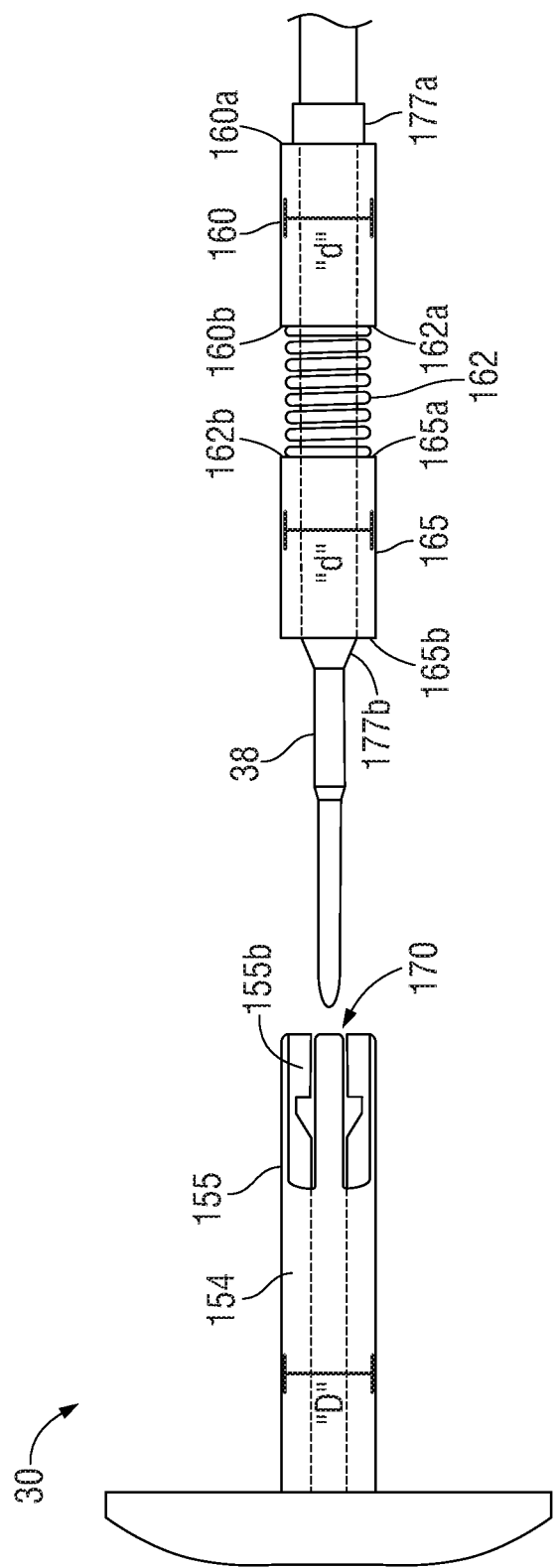
FIG. 15A is a side view of the anvil retainer, prior to being engaged to anvil assembly, in accordance with an embodiment of the present disclosure.

As shown in FIGS. 15A-15B, anvil retainer 38 may be disposed through a proximal tube 160 and a distal tube 165. Anvil retainer 38 includes a proximal annular protrusion 177a, and distal annular protrusion 177b. A resilient member 162 is disposed between proximal tube 160 and distal tube 165. A proximal end 160a of proximal tube 160 lays flush with proximal protrusion 177a such that proximal protrusion 177a restricts proximal translation of proximal tube 160. In addition, a distal end 160b of proximal tube 160 is disposed adjacent to a proximal portion 162a of resilient member 162. A distal portion 162b of resilient member 162 is disposed adjacent to a proximal end 165a of distal tube 165. Distal tube 165 is slidingly engaged with anvil retainer 38 such that distal tube 165 may translate proximally toward proximal tube 160.

The outer diameter "D" of center rod 154 may be equal to the outer diameter "d" of distal tube 165 and/or proximal tube 160. With such an arrangement, when anvil assembly 30 is engaged with anvil retainer 38, the outer perimeter of center rod 154 will lay flush with the outer perimeter of distal tube 165 and/or proximal tube 160. Additionally, or alternatively, the outer diameter "D" of center rod 154 may be less than the outer diameter "d" of distal tube 165 and/or proximal tube 160. When the outer diameter "D" of center rod 154 is less than the outer diameter "d" of distal tube 165 and/or proximal tube 160, then the outer perimeter of the center rod 154 will not lay flush with the outer perimeter of the anvil retainer 38.

Referring specifically to FIG. 15A, anvil assembly 30 is shown prior to being engaged with anvil retainer 38. This arrangement displays anvil retainer 38 in its original position where proximal tube 160 is spaced apart from distal tube 165. Resilient member 162 provides an outward force against distal end 160b of proximal tube 160 and proximal end 165a of distal tube 165. With the force applied by resilient member 162, the proximal end 160a of proximal tube 160 is resting against proximal protrusion 177a of anvil retainer 38. In addition, the distal end 165b of distal tube 165 rests against distal protrusion 177b.

Turning now to FIG. 15B, anvil assembly 30 is shown attached to anvil retainer 38. During attachment of anvil assembly 30 to anvil retainer 38, anvil retainer 38 is positioned within bore 170 of center rod 154 of anvil assembly 30. Flexible arms 155 deflect outwardly to accommodate center rod 154. Center rod 154 is advanced onto anvil retainer 38 in the direction indicated by arrow "K" until internal shoulder 155b of flexible arms 155 passes over distal annular protrusion 177b formed on anvil retainer 38. Prior to the internal shoulders 155b of flexible arms 155 passing over distal annular protrusion 177b, and upon advancement of center rod 154 onto anvil retainer 38, the proximal end 154e of center rod 154 engages with the distal end 165b of distal tube 165 such that the proximal advancement of center rod 154 translates distal tube 165 proximally toward proximal tube 160, until flexible arms 155 releasably engage the anvil retainer 38, i.e. internal shoulders 155b releasably engage with distal annular protrusion 177b.

As described above, when anvil assembly 30 is engaged with anvil retainer 38, the outer perimeter of center rod 154 of anvil assembly 30 will lay flush with the outer perimeter of distal tube 165 and/or proximal tube 160 of anvil retainer 38. The outer diameter "D" of center rod 154 may be equal to the outer diameter "d" of distal tube 165 and/or proximal tube 160. Additionally, or alternatively, the outer diameter "D" of center rod 154 may be less than the outer diameter "d" of distal tube 165 and/or proximal tube 160. When the outer diameter "D" of center rod 154 is less than the outer diameter "d" of distal tube 165 and/or proximal tube 160, then the outer perimeter of the center rod 154 will not lay flush with the outer perimeter of the anvil retainer 38.

A method of using surgical stapling device 10 will now be described with reference to FIGS. 16A-16C.

Figure 16A:
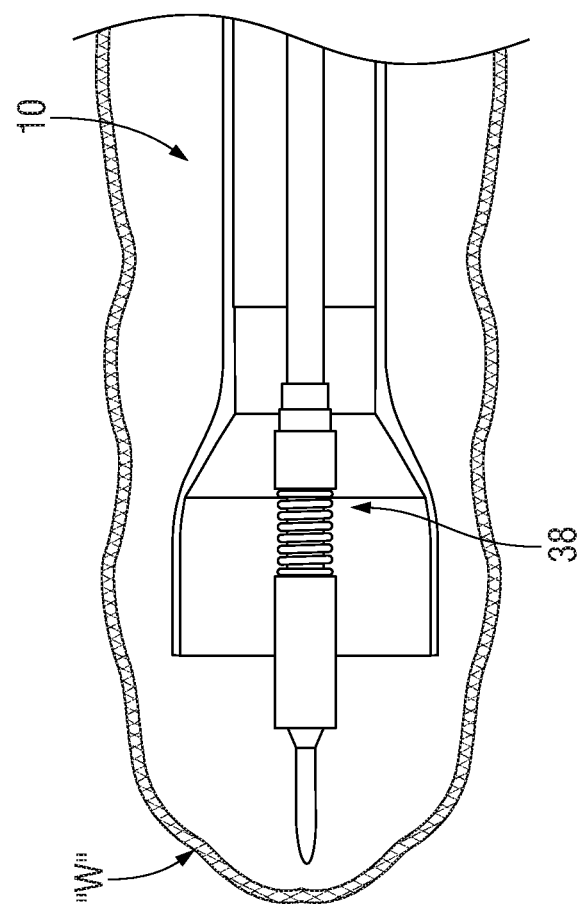
FIG. 16A illustrates the anvil retainer of FIG. 15A with the surgical device in the unapproximated or open position prior to attachment of anvil assembly to the anvil retainer.
Figure 16A:
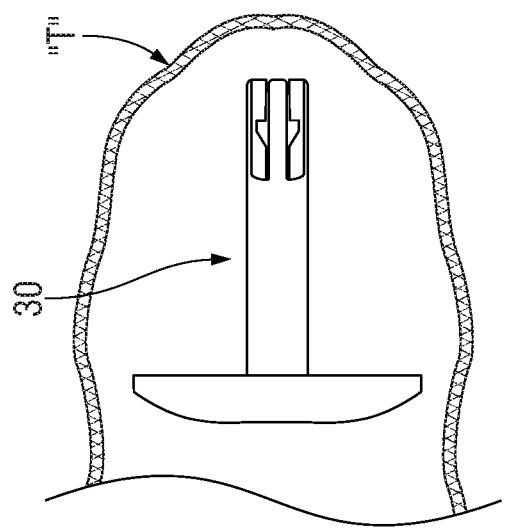

FIG. 16A illustrates surgical stapling device 10 in the unapproximated or open position prior to attachment of anvil assembly 30 to anvil retainer 38, and prior to anvil retainer 38 being pierced through tissue wall "W" and prior to anvil assembly 30 being pierced through tissue wall "T." In this position, and referring briefly to FIGS. 5 and 7, biasing member 106 is engaged with coupling 86 to urge pusher link 74 to its proximal-most position in which coupling 86 abuts screw-stop 306. Biasing member 512 is engaged with slide member 500 of the indicator mechanism to position slide member 500 in engagement with projection 518 of indicator 24 to pivot indicator 24 in a clockwise direction. Biasing member 549 is engaged with body 536 of lockout member 530 to urge lockout member 530 to its distal-most position, wherein lip portion 542 of lockout member 530 is positioned above extension 26b of trigger lock 26 to prevent movement of trigger lock 26 to the unlocked position. Biasing member 82a is also engaged with pivot member 79 to urge pivot member 79 to the base of vertical slot 82. In this position, anvil retainer 38 is urged through tissue wall "W" and anvil assembly 30 is urged through tissue wall "T." Additionally, or alternatively, tissue walls "W," "T" may be cut and opened to allow the passage of anvil retainer 38 and/or anvil assembly 30, respectively, therethrough. In this arrangement, a suture may be used to tie tissue walls "W," "T" to anvil assembly 30 and anvil retainer 38.

Turning now to FIG. 16B, surgical stapling device 10 is shown in the unapproximated position with anvil retainer 38 pierced through tissue wall "W" and anvil assembly 30 pierced through tissue wall "T." In this position, anvil assembly 30 is ready to be engaged with anvil retainer 38. As shown in FIG. 16B, tissue wall "W" surrounds the proximal tube 160 of anvil retainer 38.

Figure 16C:
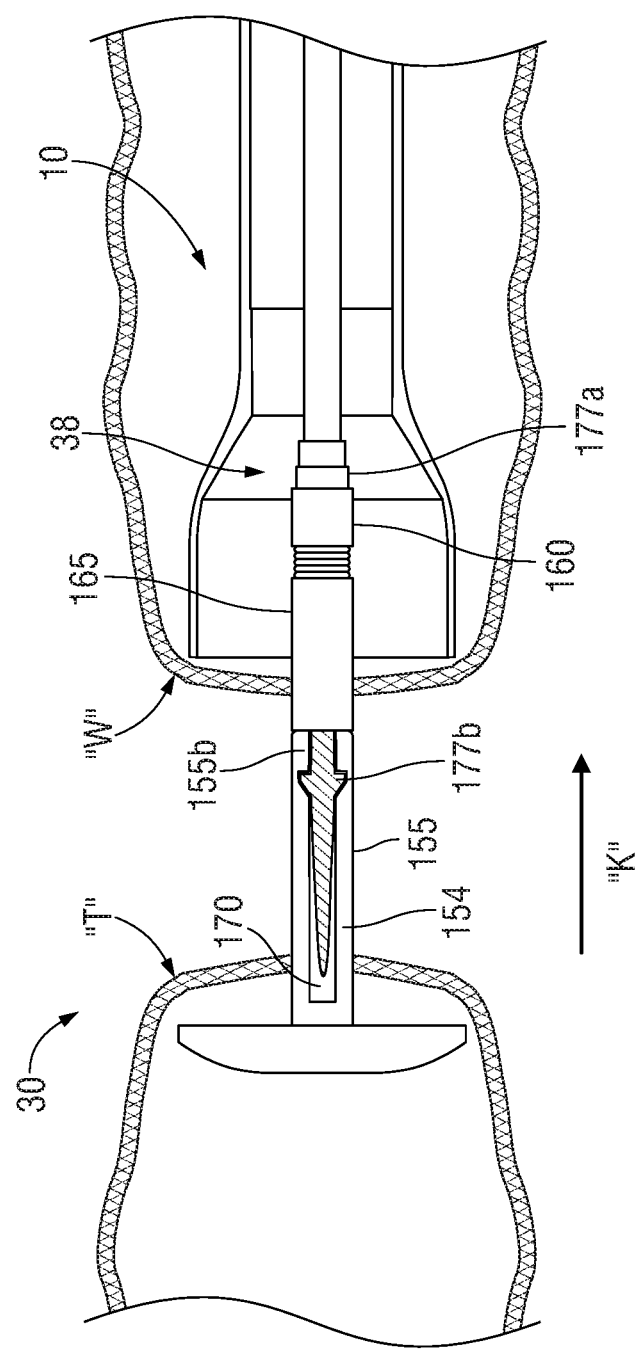
FIG. 16C is a view of the anvil retainer of FIG. 16B subsequent to engagement of anvil assembly and anvil retainer.

Turning now to FIG. 16C, surgical stapling device 10 is shown in the unapproximated position with anvil retainer 38 pierced through tissue wall "W" and anvil assembly 30 pierced through tissue wall "T" and anvil assembly 30 engaged with anvil retainer 38. As described above, during attachment of anvil assembly 30 to anvil retainer 38, anvil retainer 38 is positioned within bore 170 of center rod 154 of anvil assembly 30. Flexible arms 155 deflect outwardly to accommodate center rod 154. Center rod 154 is advanced onto anvil retainer 38 in the direction indicated by arrow "K." Advancement of center rod 154 onto anvil retainer 38 results in the proximal advancement of distal tube 165 toward proximal tube 160. Center rod 154 is advanced onto anvil retainer 38 until internal shoulder 155b of flexible arms 155 passes over distal annular protrusion 177b formed on anvil retainer 38. At this point, flexible arms 155 releasably engage the anvil retainer 38. The position of the remaining components of surgical stapling device 10 is not affected by attachment of anvil assembly 30 to anvil retainer 38 and remains as described above.

Figure 16D:
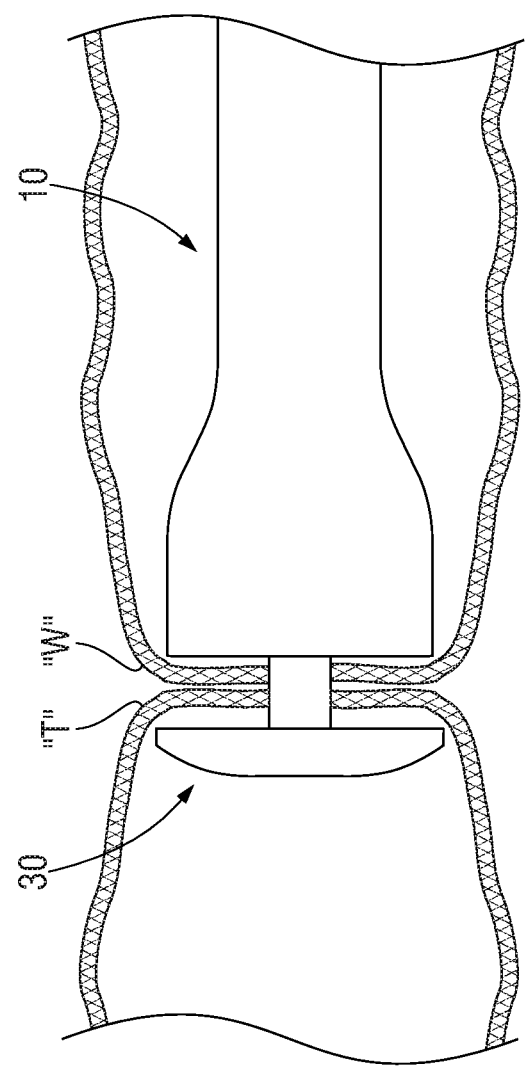
FIG. 16D is a view of the anvil retainer of FIG. 16C with the surgical device in the approximated position.

Turning now to FIG. 16D, surgical stapling device 10 is shown with anvil retainer 38 (now internal to surgical stapling device 10) attached to anvil assembly 30, and the surgical stapling device 10 in the approximated or closed position. As discussed above, and referring briefly back to FIGS. 5-8, surgical stapling device 10 is moved to the approximated or closed position by rotating rotation knob 22. Rotation of knob 22 causes cylindrical sleeve 33 to rotate to move pin 52 along helical channel 50 of screw 32. Movement of pin 52 15 along helical channel 50 causes screw 32 to translate proximally within sleeve 33. The distal end of screw 32 is connected to screw extensions 34 and 36 which are fastened at their distal ends to anvil retainer 38. As such, retraction of screw 32 within sleeve 33 is translated into 20 proximal movement of anvil retainer 38 and anvil assembly 30.

During approximation of anvil retainer 38 and anvil assembly 30 into surgical stapling device 10, tissue wall "W" slides over proximal tube 160, distal tube 165, and center rod 154 of anvil assembly 30. As described above, the outer diameter "d" of distal tube 165 and/or proximal tube 160 is either equal to or greater than the outer diameter "D" of anvil assembly 30. With the outer diameters in this configuration, tissue wall "W" may slide over center rod 154 of anvil assembly 30 and thus tissue wall "W" will refrain from being pulled into surgical stapling device 10.

Further details of other features of surgical instrument 10, such as the approximation assembly, firing assembly, and lock out mechanism are disclosed in commonly-owned U.S. Pat. Nos. 7,168,604 and 7,303,106, the entire contents of each of which are incorporated by reference herein.

It will be understood that various modifications may be made to the embodiments disclosed herein. Therefore, the above description should not be construed as limiting, but merely as exemplifications of disclosed embodiments. Those skilled in the art will envision other modifications within the scope and spirit of the claims appended hereto.

What is claimed is:

1. An anvil retaining apparatus, comprising:
   an anvil retainer including a proximal portion configured to be operatively coupled to a surgical device, and a distal portion having a surface feature configured to be coupled to an anvil; and
   a collar disposed about the anvil retainer, wherein the collar is movable relative to and along the anvil retainer between a distal position, in which the collar is disposed about the surface feature, and a proximal position, in which the surface feature is exposed.

2. The anvil retaining apparatus according to claim 1, wherein the surface feature is a protrusion or a recess.

3. The anvil retaining apparatus according to claim 1, wherein the surface feature is an annular protrusion extending outwardly from the distal portion of the anvil retainer.

4. The anvil retaining apparatus according to claim 1, wherein the collar is a distal collar and the anvil retaining apparatus further includes:
   a proximal collar; and
   a resilient member disposed between the proximal collar and the distal collar.

5. The anvil retaining apparatus according to claim 4, wherein the proximal collar remains axially stationary relative to the anvil retainer.

6. The anvil retaining apparatus according to claim 4, wherein the distal collar is slidable relative to and along the anvil retainer toward the proximal collar.

7. The anvil retaining apparatus according to claim 4, wherein the distal collar is slidable relative to and along the anvil retainer between the proximal position, in which the distal collar is disposed a first distance from the proximal collar, and the distal position, in which the distal collar is disposed a second distance from the proximal collar, greater than the first distance.

8. The anvil retaining apparatus according to claim 4, wherein the resilient member biases the distal collar toward the distal position.

9. The anvil retaining apparatus according to claim 4, wherein the resilient member is a coil spring having a proximal portion disposed adjacent a distal portion of the proximal collar, and a distal portion disposed adjacent a proximal portion of the distal collar.

10. An anvil assembly comprising:
    an anvil head;
    an anvil rod extending from the anvil head;
    an anvil retainer having a portion configured for selective coupling to a portion of the anvil rod; and
    a collar disposed about the anvil retainer and movable relative to and along the anvil retainer between a distal position, in which the portion of the anvil retainer is disposed within the collar, and a proximal position, in which the portion of the anvil retainer is disposed distally of the collar.

11. The anvil assembly according to claim 10, wherein the portion of the anvil rod is a protrusion or a recess, and the portion of the anvil retainer is the other of the protrusion or the recess.

12. The anvil assembly according to claim 11, wherein the protrusion is annular and extends outwardly from an outer surface of the anvil retainer.

13. The anvil assembly according to claim 10, wherein the anvil rod defines a longitudinally extending bore configured for receipt of the anvil retainer.

14. The anvil assembly according to claim 13, wherein the collar defines a distally-facing planar edge surface, and the anvil rod defines a proximally-facing planar edge surface configured to abut the distally-facing planar edge surface upon coupling of the anvil retainer with the anvil rod.

15. The anvil assembly according to claim 10, wherein the collar has an outer diameter substantially equal to an outer diameter of the anvil rod.

16. The anvil assembly according to claim 10, wherein the anvil rod is configured to engage and urge the collar from the distal position toward the proximal position upon proximal movement of the anvil rod relative to and along the anvil retainer.

17. The anvil assembly according to claim 10, wherein the collar is a distal collar and the anvil assembly further includes:
   a proximal collar; and
   a resilient member disposed between the proximal collar and the distal collar.

18. The anvil assembly according to claim 17, wherein the distal collar is slidable relative to and along the anvil retainer toward the proximal collar.

19. The anvil assembly according to claim 17, wherein the resilient member biases the distal collar toward the distal position.

20. The anvil assembly according to claim 10, wherein the portion of the anvil retainer is concealed within the collar when the collar is in the distal position, and the portion of the anvil retainer is disposed outside of the collar when the collar is in the proximal position.

* * * * *